(12) United States Patent
Sase

(10) Patent No.: US 9,946,058 B2
(45) Date of Patent: Apr. 17, 2018

(54) MICROSCOPE APPARATUS AND OBSERVATION METHOD

(75) Inventor: Ichiro Sase, Tokyo (JP)

(73) Assignee: NIKON CORPORATION, Tokyo (JP)

(*) Notice: Subject to any disclaimer, the term of this patent is extended or adjusted under 35 U.S.C. 154(b) by 421 days.

(21) Appl. No.: 13/157,805

(22) Filed: Jun. 10, 2011

(65) Prior Publication Data

US 2012/0062722 A1 Mar. 15, 2012

(30) Foreign Application Priority Data

Jun. 11, 2010 (JP) ................. P2010-134217

(51) Int. Cl.
*G02B 21/16* (2006.01)
*G01N 21/64* (2006.01)
(Continued)

(52) U.S. Cl.
CPC ......... *G02B 21/16* (2013.01); *G01N 21/6458* (2013.01); *G02B 21/367* (2013.01); *G02B 21/06* (2013.01); *G02B 27/56* (2013.01)

(58) Field of Classification Search
USPC .......................................................... 348/79
See application file for complete search history.

(56) References Cited

U.S. PATENT DOCUMENTS 3,891,853 A * 6/1975 Kremen ................ G01J 3/4406
250/458.1
4,375,163 A * 3/1983 Yang ............................ 73/61.53
(Continued)

FOREIGN PATENT DOCUMENTS

DE 10 2008 059 328 A1 6/2010
JP A-2005-09969 1/2005
(Continued)

OTHER PUBLICATIONS

Aug. 13, 2013 Office Action issued in Japanese Patent Application No. 2012-519446 (with translation).
(Continued)

*Primary Examiner* — Peter D Le
(74) *Attorney, Agent, or Firm* — Oliff PLC

(57) ABSTRACT

A microscope apparatus comprises: a distribution measurement apparatus which—with respect to an observation region wherein a sample is arranged which comprises a fluorescent material that is activated when irradiated with an activating light of a prescribed wavelength, and that emits fluorescence when irradiated in an activated condition with an exciting light of a wavelength that differs from that of the activating light—obtains a fluorescent picture image by conducting irradiation with the exciting light, and measures a fluorescent intensity distribution of the observation region; an irradiation intensity setting apparatus which sets irradiation intensities of the activating light for respective portions of the observation region based on the fluorescent intensity distribution; and a picture image formation apparatus which obtains a plurality of the fluorescent picture images by multiply repeating operations comprising an operation wherein the observation region is irradiated with the activating light at the irradiation intensities that have been set in the respective portions, and an operation wherein a fluorescent picture image is obtained by irradiating the observation region with the exciting light after the activating light irradiation, and which generates a sample picture image from the plurality of the fluorescent picture images.

15 Claims, 11 Drawing Sheets

(51) Int. Cl.
   *G02B 21/36*   (2006.01)
   *G02B 21/06*   (2006.01)
   *G02B 27/56*   (2006.01)

(56) References Cited

U.S. PATENT DOCUMENTS

| | | | | |
|---|---|---|---|---|
| 4,917,491 | A * | 4/1990 | Ring | G01N 21/7703 250/227.23 |
| 5,332,905 | A * | 7/1994 | Brooker | G01J 3/2823 250/361 C |
| 5,759,444 | A * | 6/1998 | Enokida | C07C 211/61 252/301.16 |
| 6,396,053 | B1 * | 5/2002 | Yokoi | 250/234 |
| 6,464,633 | B1 * | 10/2002 | Hosoda | A61B 1/0638 348/68 |
| 6,855,941 | B1 * | 2/2005 | Tomioka | 250/483.1 |
| 8,129,685 | B2 * | 3/2012 | Nakamura et al. | 250/361 R |
| 2002/0196337 | A1 * | 12/2002 | Takeyama | A61B 1/0638 348/131 |
| 2004/0051051 | A1 | 3/2004 | Kato et al. | |
| 2005/0122579 | A1 * | 6/2005 | Sasaki | G02B 21/0044 359/385 |
| 2006/0020169 | A1 * | 1/2006 | Sugimoto | A61B 1/00009 600/180 |
| 2006/0025692 | A1 * | 2/2006 | Ishihara | 600/478 |
| 2007/0093691 | A1 * | 4/2007 | Kobayashi | 600/180 |
| 2007/0272885 | A1 * | 11/2007 | Yamashita et al. | 250/585 |
| 2007/0295892 | A1 | 12/2007 | Kanegae et al. | |
| 2008/0032414 | A1 * | 2/2008 | Zhuang et al. | 436/172 |
| 2008/0068588 | A1 | 3/2008 | Hess et al. | |
| 2009/0179159 | A1 * | 7/2009 | Yamada | 250/459.1 |
| 2009/0206251 | A1 | 8/2009 | Hess et al. | |
| 2009/0231692 | A1 * | 9/2009 | Yoshida et al. | 359/385 |
| 2009/0237501 | A1 * | 9/2009 | Lemmer et al. | 348/79 |
| 2011/0121200 | A1 * | 5/2011 | Watanabe | 250/458.1 |
| 2011/0226965 | A1 | 9/2011 | Wolleschensky et al. | |
| 2011/0242308 | A1 * | 10/2011 | Igarashi et al. | 348/79 |

FOREIGN PATENT DOCUMENTS

| | | |
|---|---|---|
| JP | A-2008-09395 | 1/2008 |
| JP | A-2008-26885 | 2/2008 |
| JP | A-2008-542826 | 11/2008 |
| JP | A-2009-115891 | 5/2009 |
| WO | WO 02/48693 A1 | 6/2002 |
| WO | WO 2006/127692 A2 | 11/2006 |
| WO | 2009/141410 A1 | 11/2009 |

OTHER PUBLICATIONS

Betzig, "Proposed method for molecular optical imaging," *Optics Letters*, Feb. 1, 1995, pp. 237-239, vol. 20, No. 3, Optical Society of America.

Van De Linde et al., "Photoswitching microscopy with standard fluorophores," *Applied Physics B*, Oct. 19, 2008, pp. 725-731, vol. 93, Springer.

Sep. 20, 2011 Written Opinion issued in International Patent Application No. PCT/JP2011/063474 (with translation).

Sep. 20, 2011 International Search Report issued in International Patent Application No. PCT/JP2011/063474 (with translation).

Aug. 15, 2014 Office Action issued in Chinese Application No. 201180028431.3 (with translation).

Hess, S. T. et al.: "Ultra-high Resolution Imaging by Fluorescence Photoactivation Localization Microscopy", Biophysical Journal, Elsevier, Amsterdam, NL, vol. 91, No. 11, Dec. 31, 2006 (Dec. 31, 2006), pp. 4258-4272, XP008082813, ISSN: 0006-3495, DOI: 10.1529/Biophysj.106.091116.

Oct. 24, 2017 Search Report issued in European Application No. 11792583.4.

\* cited by examiner

IN THE CASE OF A SINGLE MOLECULE

FLUORESCENT
BRIGHT SPOT

DETECTION PULSE

IN THE CASE WHERE TWO MOLECULES
ARE CLOSE TOGETHER

FLUORESCENT
BRIGHT SPOTS

DETECTION PULSE

IN THE CASE WHERE TWO MOLECULES
ARE PROPERLY SEPARATED

FLUORESCENT
BRIGHT SPOTS

DETECTION PULSE

MICROSCOPE APPARATUS AND OBSERVATION METHOD

CROSS-REFERENCE TO RELATED APPLICATION

Priority is claimed on Japanese Patent Application No. 2010-134217, filed on Jun. 11, 2010, the contents of which are incorporated herein by reference.

BACKGROUND

Field of the Invention

The present invention relates to a microscope apparatus and an observation method.

Description of Related Art

Previously, as a super-resolution microscope, STORM (Stochastic Optical Reconstruction Microscopy) has been known (e.g., see US Patent Publication No. 2008/0032414). With this microscope, as an observation sample, one uses fluorescent material or an object to which this fluorescent material adheres which is activated when irradiated with activating light of a prescribed wavelength, and which has the property of becoming inactive by emitting fluorescence when subsequently irradiated with exciting light of a wavelength that differs from the activating light. With respect to this type of observation sample, the fluorescent material is activated at low density by irradiation with weak activating light, and a fluorescent picture image is obtained by subsequently conducting irradiation with exciting light to cause the fluorescent material to emit light. In a fluorescent picture image obtained in this manner, fluorescent bright spots (images of fluorescent material) are arranged at low density, and are individually isolated, thereby enabling obtainment of the center-of-gravity positions of the individual images. The steps in which such fluorescent picture images are obtained are repeated, for example, multiple times—e.g., several hundred to several tens of thousands of times—enabling obtainment of sample picture images of high-resolution by conducting image processing which synthesizes the multiple fluorescent picture images that are obtained.

SUMMARY

With respect to the conventional observation method, in the case where multiple regions with markedly different densities of fluorescent material exist within the same view field, a picture image of high resolution cannot be obtained, because it is not possible to separately detect individual fluorescent bright spots at sites where fluorescent material is disposed at high density, The object of the aspects of the present invention is to offer a microscope apparatus capable of obtaining picture images of high resolution even in cases of bias in the distribution of fluorescent material within the same view field, and an observation method.

Certain aspects of the present invention offer a microscope apparatus and observation method pertaining to samples as follows.

That is, a microscope apparatus pertaining to one aspect of the present invention includes: a distribution measurement apparatus which—with respect to an observation region wherein a sample is arranged which comprises fluorescent material that is activated when irradiated with an activating light of a prescribed wavelength, and that emits fluorescence when irradiated in an activated condition with an exciting light of a wavelength that differs from that of the activating light—obtains a fluorescent picture image by conducting irradiation with the exciting light, and measures a fluorescent intensity distribution of the observation region; an irradiation intensity setting apparatus which sets irradiation intensities of the activating light that irradiates the observation region based on the fluorescent intensity distribution; and a picture image formation apparatus which obtains a plurality of the fluorescent picture images by multiply repeating operations including an operation wherein the observation region is irradiated with the activating light at the irradiation intensities that have been set, and an operation wherein the observation region is irradiated with the exciting light to obtain a fluorescent picture image, and which generates a sample picture image from the plurality of the fluorescent picture images.

In addition, a microscope apparatus pertaining to one aspect of the present invention includes: a distribution measurement apparatus which—with respect to an observation region wherein a sample is arranged which comprises a fluorescent material that spontaneously flickers when irradiated with an exciting light of a prescribed wavelength—obtains a fluorescent picture image by conducting irradiation with the exciting light, and measures a fluorescent intensity distribution of the observation region; an irradiation intensity setting apparatus which sets irradiation intensities of the exciting light that irradiates the observation region based on the fluorescent intensity distribution; and a picture image formation apparatus which obtains a plurality of the fluorescent picture images by multiply repeating operations including an operation wherein the observation region is irradiated with the exciting light at the irradiation intensities that have been set, and an operation wherein a fluorescent picture image is obtained that has been excited by the exciting light of the observation region, and which generates a sample picture image from the plurality of the fluorescent picture images.

In addition, a microscope apparatus pertaining to one aspect of the present invention includes: a distribution measurement apparatus which—with respect to an observation region wherein a sample is arranged which comprises a fluorescent material that is activated when irradiated with an activating light of a prescribed wavelength, and that emits fluorescence when irradiated in an activated condition with an exciting light of a wavelength that differs from that of the activating light—obtains a fluorescent picture image by conducting irradiation with the exciting light, and measures a fluorescent intensity distribution of the observation region; an irradiation intensity setting apparatus which sets irradiation intensities of the activating light for respective portions of the observation region based on the fluorescent intensity distribution; and a picture image formation apparatus which obtains a plurality of the fluorescent picture images by alternately and multiply repeating an operation wherein the observation region is irradiated with the activating light at the irradiation intensities that have been set in respective portions, and an operation wherein a fluorescent picture image is obtained by irradiating the observation region with the exciting light after the activating light irradiation, and which generates a sample picture image from the plurality of the fluorescent picture images.

In addition, a microscope apparatus pertaining to one aspect of the present invention includes: a distribution measurement apparatus which—with respect to an observation region wherein a sample is arranged which comprises a fluorescent material that spontaneously flickers when irradiated with an exciting light of a prescribed wavelength— obtains a fluorescent picture image by conducting irradiation with the exciting light, and measures a fluorescent intensity distribution of the observation region; an irradiation intensity setting apparatus which sets irradiation intensities of the exciting light for respective portions of the observation region based on the fluorescent intensity distribution; and a picture image formation apparatus which obtains a plurality of the fluorescent picture images by alternately and multiply repeating an operation wherein the observation region is irradiated with the exciting light at the irradiation intensities that have been set in respective portions, and an operation wherein a fluorescent picture image is obtained that has been excited by the exciting light of the observation region, and which generates a sample picture image from the plurality of the fluorescent picture images.

In addition, an observation method pertaining to one aspect of the present invention includes: a distribution measurement step wherein—with respect to an observation region wherein a sample is arranged which comprises a fluorescent material that is activated when irradiated with an activating light of a prescribed wavelength, and that emits fluorescence when irradiated in an activated condition with an exciting light of a wavelength that differs from that of the activating light—a fluorescent picture image is obtained by conducting irradiation with the exciting light, and a fluorescent intensity distribution of the observation region is measured; an irradiation intensity setting step wherein irradiation intensities of the activating light that irradiates the observation region are set based on the fluorescent intensity distribution; and a picture image formation step wherein a plurality of the fluorescent picture images is obtained by multiply repeating operations including an operation in which the observation region is irradiated with the activating light at the irradiation intensities that have been set, and an operation in which a fluorescent picture image is obtained by irradiating the observation region with the exciting light, and wherein a sample picture image is generated from the plurality of the fluorescent picture images.

In addition, an observation method pertaining to one aspect of the present invention includes: a distribution measurement step wherein—with respect to an observation region wherein a sample is arranged which comprises a fluorescent material that spontaneously flickers when irradiated with an exciting light of a prescribed wavelength—a fluorescent picture image is obtained by conducting irradiation with the exciting light, and a fluorescent intensity distribution of the observation region is measured; an irradiation intensity setting step wherein irradiation intensities of the exciting light that irradiates the observation region are set based on the fluorescent intensity distribution; and a picture image formation step wherein a plurality of the fluorescent picture images is obtained by multiply repeating operations including an operation in which the observation region is irradiated with the exciting light at the irradiation intensities that have been set, and an operation in which a fluorescent picture image is obtained that has been excited by the exciting light of the observation region, and wherein a sample picture image is generated from the plurality of the fluorescent picture images.

In addition, an observation method pertaining to one aspect of the present invention includes: a distribution measurement step wherein—with respect to an observation region wherein a sample is arranged which comprises a fluorescent material that is activated when irradiated with an activating light of a prescribed wavelength, and that emits fluorescence when irradiated in an activated condition with an exciting light of a wavelength that differs from that of the activating light—a fluorescent picture image is obtained by conducting irradiation with the exciting light, and a fluorescent intensity distribution of the observation region is measured; an irradiation intensity setting step wherein irradiation intensities of the activating light for respective portions of the observation region are set based on the fluorescent intensity distribution; and a picture image formation step wherein a plurality of the fluorescent picture images is obtained by multiply repeating operations including an operation in which the observation region is irradiated with the activating light at the irradiation intensities that have been set in the respective portions, and an operation in which a fluorescent picture image is obtained by irradiating the observation region with the exciting light, and wherein a sample picture image is generated from the plurality of the fluorescent picture images.

In addition, an observation method pertaining to one aspect of the present invention includes: a distribution measurement step wherein—with respect to an observation region wherein a sample is arranged which comprises a fluorescent material that spontaneously flickers when irradiated with an exciting light of a prescribed wavelength—a fluorescent picture image is obtained by conducting irradiation with the exciting light, and a fluorescent intensity distribution of the observation region is measured; an irradiation intensity setting step wherein irradiation intensities of the exciting light are set for respective portions of the observation region based on the fluorescent intensity distribution; and a picture image formation step wherein a plurality of the fluorescent picture images is obtained by multiply repeating operations including an operation in which the observation region is irradiated with the exciting light at the irradiation intensities that have been set in the respective portions, and an operation in which a fluorescent picture image is obtained that has been excited by the exciting light of the observation region, and wherein a sample picture image is generated from the plurality of the fluorescent picture images.

According to the microscope apparatus and observation method pertaining to the aspects of the present invention, picture images of high resolution can be obtained even in cases of large bias in the distribution of fluorescent material within the same view field.

DESCRIPTION OF EMBODIMENTS

Descriptions are given below concerning individual embodiments of a microscope apparatus and a method of observation of samples, with reference to drawings. The present embodiments are specifically described for the purpose of better comprehending the intent of the present invention, and do not limit the present invention unless otherwise indicated. With respect to the drawings used in the following descriptions, there are cases where some of the main components are shown with enlargement for purposes of convenience in order to facilitate comprehension of properties, and dimensional proportions and the like are not necessarily identical to the actual.

First Embodiment

Figure 1:
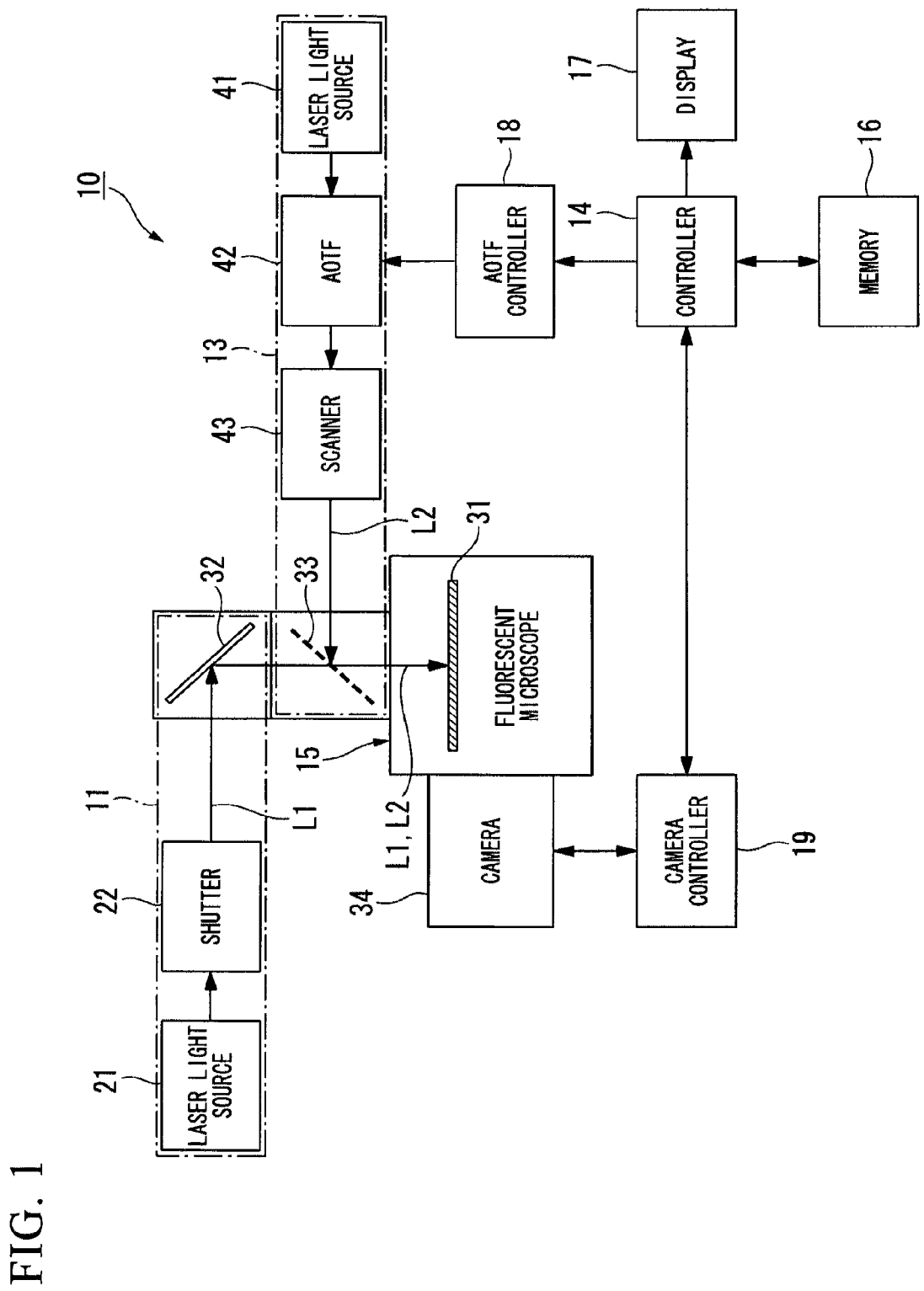
FIG. 1 is a block diagram showing a first embodiment of the microscope apparatus.

FIG. 1 is a schematic view which shows a microscope apparatus pertaining to a first embodiment.

A microscope apparatus 10 is provided with a microscope body 15, an excitation illumination system 11 attached to the microscope body 15, an activation illumination system 13, a controller 14, a memory 16, and a display 17.

The microscope apparatus 10 is a microscope apparatus which uses super-resolution microscopy (stochastic optical reconstruction microscopy: STORM).

In the microscope apparatus 10, a sample is used which is provided with inactive fluorescent material as a label that is activated when irradiated with activating light L2 of a prescribed wavelength, and that emits fluorescence when irradiated in an activated condition with exciting light L1 of a wavelength that differs from the activating light L2. Using the excitation illumination system 11 and the activation illumination system 13, one repeats operations wherein discretely distributed fluorescence is observed by causing light emission of only a portion of the fluorescent material in the sample, and a sample picture image is formed using the numerous fluorescent picture images obtained thereby.

The microscope body 15 is, for example, an inverted microscope. The microscope body 15 is provided with a stage 31 upon which a sample that is the object of observation is mounted, and is connected to a total reflection mirror 32 which reflects exciting light L1 that is radiated from a laser light source 21 toward the stage 31, a dichroic mirror 33 which reflects activating light L2 that is radiated from a below-mentioned laser light source 41 toward the stage 31, and which transmits the exciting light L1, and a camera 34 which picks up a fluorescent picture image of the sample that is mounted on the stage 31.

Although not illustrated in the drawings, the microscope body 15 is also provided with an objective lens which irradiates the stage 31 with the exciting light L1 and the activating light L2, an imaging lens which couples the fluorescence (observation light) from the sample to the light receiving surface of the camera 34, and the like.

The stage 31 is configured to enable total reflection illumination that causes total reflection of the exciting light L1 and the activating light L2 at the interface of a sample and a cover glass affixed to the sample. According to total reflection illumination, the sample can be illuminated by the evanescent light that exudes from the cover glass to the sample side when the illuminating light (exciting light L1 or activating light L2) is totally reflected. As the range that evanescent light travels is limited to a range on the order of 100-150 nm from the interface, only the fluorescent material positioned in the vicinity of the cover glass surface can be induced to emit light, and this can be achieved with a high S/N ratio by markedly mitigating background fluorescence.

The microscope body 15 of the present embodiment has a configuration that enables use by switching between the aforementioned total reflection illumination and ordinary epi-illumination.

The excitation illumination system 11 is provided with a laser light source 21, a shutter 22, and a total reflection mirror 32, and is connected to the microscope body 15 via the total reflection mirror 32.

The laser light source 21 is a light source which supplies exciting light L1 to the microscope body 15 for the purpose of causing light emission of the fluorescent material imparted to the sample. The laser light source 21 may emit the exciting light L1 in a wavelength adapted to the fluorescent material contained in the sample. For example, according to the type of fluorescent material, it may use a green laser (of 532 nm wavelength), a red laser (of 633 nm, 657 nm wavelength), a violet laser (of 405 nm wavelength), a blue laser (of 457 nm wavelength), or the like.

The shutter 22 is a device which conducts changeover between supply and stoppage of exciting light L1 to the microscope body 15. For example, it may be configured to be provided with a light shielding member which blocks the exciting light L1 that is emitted from the laser light source 21, and a drive apparatus which advances and retracts this light shielding member relative to and from the optical path of the exciting light L1. Or, as the shutter 22, one may adopt an AOTF (Acousto-Optic Tunable Filter).

The excitation illumination system 11 is configured so as to irradiate the entire area of the observation view field (observation region) of the stage 31 with the exciting light L1.

The activation illumination system 13 is provided with a dichroic mirror 33, a laser light source 41, an AOTF 42, and a scanner 43, and the activation illumination system 13 and the microscope body 15 are connected by insertion of the dichroic mirror 33 into the optical path of the exciting light L1.

The laser light source 41 radiates the activating light L2 toward the microscope body 15 for purposes of activating the fluorescent material. The laser light source 41 may emit the activating light L2 in a wavelength adapted to the fluorescent material contained in the sample. For example, according to the type of fluorescent material, it may use a green laser (of 532 nm wavelength), a red laser (of 633 nm, 657 nm wavelength), a violet laser (of 405 nm wavelength), a blue laser (of 457 nm wavelength), or the like.

The AOTF 42 is an acousto-optic tunable filter, and has the function of causing spectropolarization of the activating light L2 received from the laser light source 41 by imparting ultrasonic waves from an ultrasonic wave oscillator to a doubly refracting crystal of, for example, tellurium dioxide, utilizing dilatational waves produced within this doubly refracting crystal. The AOTF 42 controls the intensity of the activating light L2 received from the laser light source 41 to a preset value, and conducts emission toward a scanner 43.

The scanner 43 scans the activating light L2 on the stage 31 of the microscope body 15. As the scanner 43, one may use, for example, a biaxial galvano scanner.

The activating illumination system 13 is configured to enable irradiation of the observation view field (observation region) on the stage 31 with the activating light L2 at irradiation intensities that are modulated by the AOTF 42 while scanning is conducted by the scanner 43.

The controller 14 is a computer which comprehensively controls the microscope apparatus 10, and is connected to the memory 16, the display 17, an AOTF controller 18, and a camera controller 19. In the present embodiment, the controller 14 has at least a control signal generation function which generates control signals for purposes of controlling these apparatus, a fluorescent picture image obtainment function which obtains fluorescent picture images via the camera controller 19, a picture image analyzing function which analyzes the obtained fluorescent picture images, and a picture image formation function which generates a sample picture image from the multiple fluorescent picture images.

The memory 16 is composed, for example, from a semiconductor memory or hard disk or the like, and stores a program used in the controller 14 and data (fluorescent picture images and the like) supplied from the controller 14 in a manner that allows read-out from the controller 14.

The display 17 is, for example, a monitor (display device) or printer (printing device). It displays images based on the picture image data outputted from the controller 14, and offers a printing function.

The AOTF controller 18 conducts drive control of the AOTF 42 that is provided in the activation illumination system 13. The AOTF controller 18 drives the AOTF 42 based on control signals inputted from the controller 14, and modulates the activating light L2 outputted from the laser light source 41.

The camera controller 19 conducts drive control of the camera 34 connected to the microscope body 15. The camera controller 19 operates the camera 34 based on control signals inputted from the controller 14, obtains picture images of the fluorescence that is radiated from the sample, and outputs the obtained fluorescent picture images to the controller 14.

Otherwise, in the excitation illumination system 11, it is also acceptable to provide an AOTF between the shutter 22 and the total reflection mirror 32. In the activation illumination system 13, one may also provide a shutter between, for example, the AOTF 42 and the scanner 43.

Furthermore, one may also employ a laser light source apparatus which is configured to provide the laser light source 21 and the laser light source 41 in a single housing, and to enable emission of multiple types of laser light. In the case where this type of laser light source apparatus is provided, both exciting light L1 and activating light L2 can be supplied to the microscope body 15 from a single illumination system by configuring an illumination system that is provided with the shutter 22, AOTF 42 and scanner 43 together with the laser light source apparatus.

The microscope apparatus 10 implements the various types of operations which are required to execute the below-mentioned observation method by performing in combination the aforementioned functions with which the controller 14 is provided. Accordingly, the microscope apparatus 10 is additionally provided with the functions of a distribution measurement apparatus which measures fluorescent intensity distribution according to the distribution of fluorescent material, an irradiation intensity setting apparatus which sets irradiation intensities of activating light in the respective portions of the observation region, and a picture image formation apparatus which generates a sample picture image by STORM photographic processing and image processing.

Next, a description is given of an observation method using the microscope apparatus 10.

Figure 2:
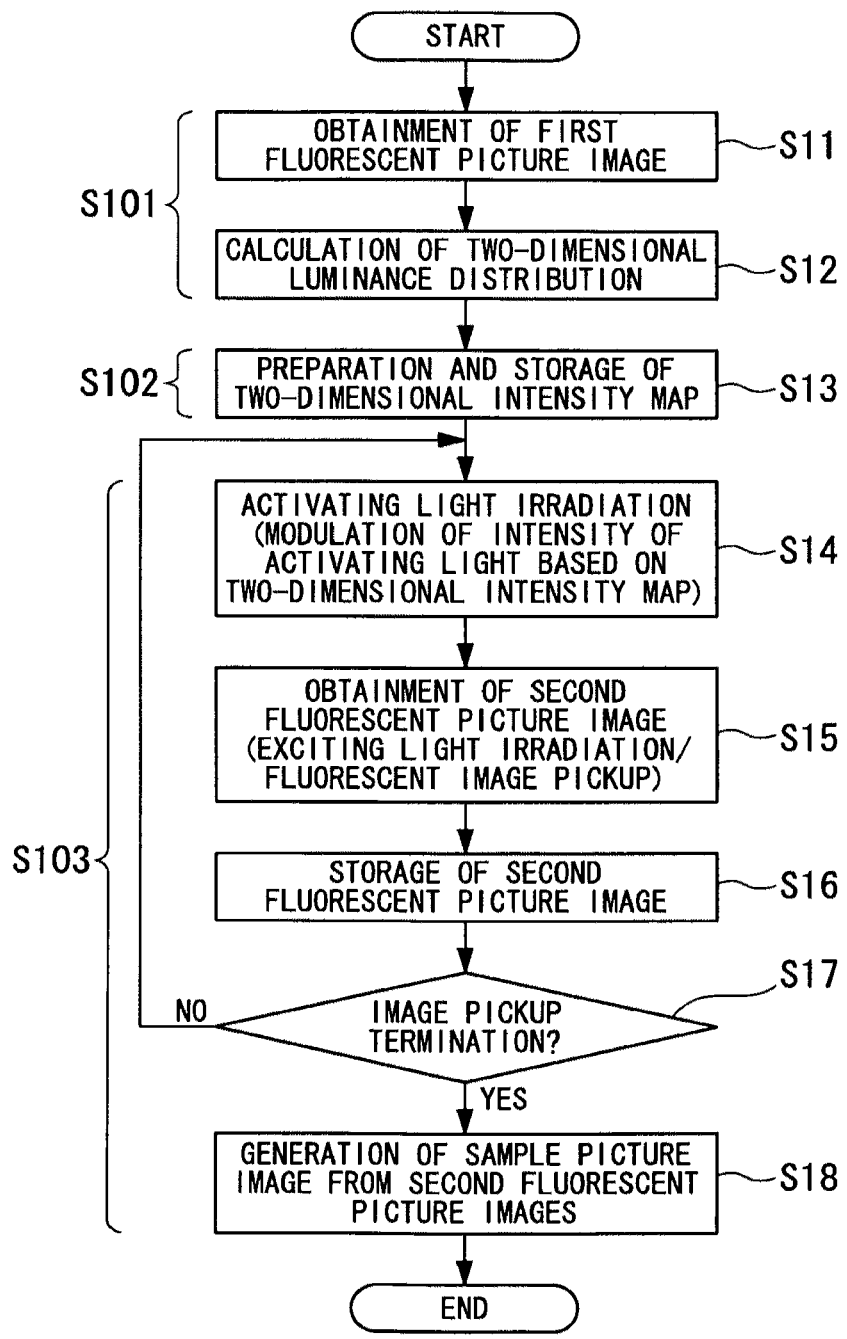
FIG. 2 is a flowchart showing an observation method of the first embodiment.

FIG. 2 is a flowchart which shows the observation method of the present embodiment. The observation method of the present embodiment is composed of a distribution measurement step S101, an irradiation intensity setting step S102, and a picture image formation step S103.

The distribution measurement step S101 includes a step S11 in which a first fluorescent picture image is obtained in the microscope apparatus 10, and a step S12 in which a two-dimensional luminance distribution (fluorescent intensity distribution) of the first fluorescent picture image is calculated.

The irradiation intensity setting step S102 includes a step S13 in which a two-dimensional intensity map (irradiation intensity distribution) of the activating light L2 is set based on the aforementioned fluorescent intensity distribution.

The picture image formation step S103 includes a step S14 in which a sample is irradiated with activating light L2 whose irradiation intensities are controlled based on the two-dimensional intensity map, a step S15 in which a second fluorescent picture image is obtained by irradiating the sample with exciting light L1, a step S16 in which a second fluorescent picture image is stored, a step S17 in which imaging termination is determined, and a step S18 in which a sample picture image is generated from multiple second fluorescent picture images.

A summary of the observation procedure is as follows.

First, in the distribution measurement step S101, a two-dimensional luminance distribution is apprehended which corresponds to the density with which fluorescent material exists in the sample. Subsequently, in the irradiation intensity setting step S102, one sets the irradiation intensity of activating light L2 in each region of the sample based on the two-dimensional luminance distribution (drafting of two-dimensional intensity map). Thereafter, in the picture image formation step S103, one repeats from several hundred times to several tens of thousands of times an operation in which the sample is irradiated while modulating the intensities of the activating light L2 based on the two-dimensional intensity map, and an operation in which a second fluorescent picture image is obtained by conducting irradiation with the exciting light L1 (STORM photographic processing). A sample picture image of high resolution is then obtained by synthesizing the numerous second fluorescent picture images that have been taken (STORM picture image processing).

The procedure in each step is described in detail below.

First, a sample imparted with fluorescent material as a label is set on the stage 31 of the microscope apparatus 10. The sample to be observed is, for example, a cell or the like that has been immersed in a culture solution.

As the fluorescent material, one uses fluorescent material which is activated when irradiated with activating light of a prescribed wavelength, and which emits fluorescence and becomes inactive when irradiated in an activated condition with exciting light of a wavelength that differs from that of the activating light. Specifically, one may use the material described in the specification of U.S. Patent Publication No. 2008/0032414, for example, one may use a dye pair that combines two types of cyanine dyes (a Cy2-Cy5 dye pair, a Cy3-Cy5 dye pair, or the like).

With respect to the aforementioned dye pairs, one of the dyes (a first dye) forms an optical radiation portion which emits light by means of exciting light, and the other dye (a second dye) either activates the first dye in response to optical irradiation, or forms an activation portion which functions as a switch to conduct changeover of the condition of the first dye. For example, with the dye pair Cy3-Cy5, Cy5 is the optical radiation portion, and Cy3 is the activation portion which enables activation of Cy5. Accordingly, when fluorescent material including the dye pair Cy3-Cy5 is irradiated with a green laser (532 nm) that corresponds to the absorption wavelength of Cy3, Cy5 which is the optical radiation portion is activated, and Cy5 transitions to a fluorescent state. When the fluorescent material in which Cy5 is in a fluorescent state is then irradiated with a red laser (633 nm) that corresponds to the absorption wavelength of Cy5, Cy5 emits light, and returns to an inactive state (dark state).

With STORM, by controlling switching operations between a fluorescent state and a dark state of the fluorescent material, it is possible to cause selective light emission of only a very small portion of the fluorescent material imparted to the sample, enabling detection of fluorescent material on the level of a single molecule.

When setting of the sample on the stage 31 is completed, the controller 14 initiates the distribution measurement step S101. In the distribution measurement step S101, first, step S11 is performed in which a first fluorescent picture image is obtained.

In step S11, first, activating light L2 which is emitted from the activation illumination system 13 is supplied to the microscope body 15, and the sample on the stage 31 is irradiated with the activating light L2. At this time, exciting light L1 is intercepted by closing the shutter 22 of the excitation illumination system 11, and the microscope body 15 receives only the activating light L2. Moreover, by means of the AOTF controller 18 which operates based on control signals inputted from the controller 14, the AOTF 42 is set to a state wherein the activating light L2 received from the laser light source 41 is outputted at a fixed intensity. The activating light L2 is then scanned over the entire observation view field by the scanner 43, and the sample is irradiated with activating light L2 of uniform intensity over the entire view field. As a result, the fluorescent material contained in the sample is activated across the entire view field. For example, in the case where the fluorescent material has the dye pair Cy3-Cy5, Cy5 which is the optical radiation portion transitions to a fluorescent state, entering a condition that enables light emission.

The sample may be irradiated with activating light L2 by either the total reflection illumination mode or the epi-illumination mode.

Figure 3:
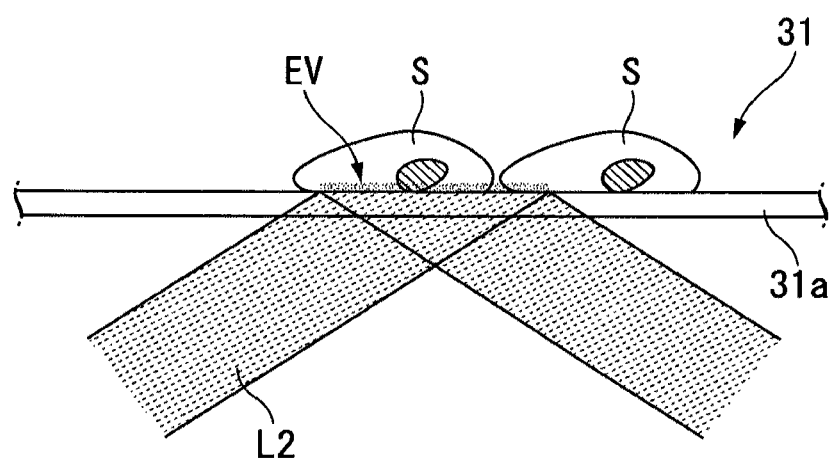
FIG. 3 is a pattern diagram of total-reflection illumination.

FIG. 3 is an explanatory view which shows the case where a sample S is irradiated with the activating light L2 (or the exciting light L1) by total reflection illumination. As shown in FIG. 3, the sample S is arranged on the cover glass 31a of the stage 31, and the activating light L2 is obliquely received at the surface of the cover glass 31a from underneath the cover glass 31a. The activating light L2 is then totally reflected at the interface of the cover glass 31a and the sample S, and evanescent light EV that exudes from the aforementioned interface to the sample S side irradiates the surface layer of the sample S on the interface side. By this means, only the fluorescent material that is positioned on the actual surface layer portion of the sample S is selectively activated.

On the other hand, in the case of epi-illumination, the activating light L2 is received in the normal direction of the cover glass 31a, and the sample S is irradiated with the activating light L2 that passes through the cover glass 31a. In this case, the entirety of the sample S in the thickness direction is irradiated with the activating light L2.

Next, a condition is entered wherein the activating illumination system 13 does not emit activating light L2, the shutter 22 of the excitation illumination system 11 is opened, and exciting light L1 that is emitted from the laser light source 21 is supplied to the microscope body 15 via the total reflection mirror 32. With the microscope apparatus 10 of the present embodiment, the exciting light L1 that is supplied from the excitation illumination system 11 irradiates the entire observation view field, whereupon the fluorescent material that has been activated by the activating light L2 emits fluorescence due to the irradiation with exciting light L1, and transitions to an inactive state. This fluorescence that is emitted by the fluorescent material is photographed by operating the camera 34 via the camera controller 19, thereby enabling obtainment of a first fluorescent picture image. The photographed first fluorescent picture image is sent to the controller 14 from the camera controller 19, and the controller 14 stores the first fluorescent picture image as necessary in the memory 16.

Next, in step S12, a two-dimensional luminance distribution (fluorescent intensity distribution) of a first fluorescent picture image is computed in the controller 14.

Figure 4:
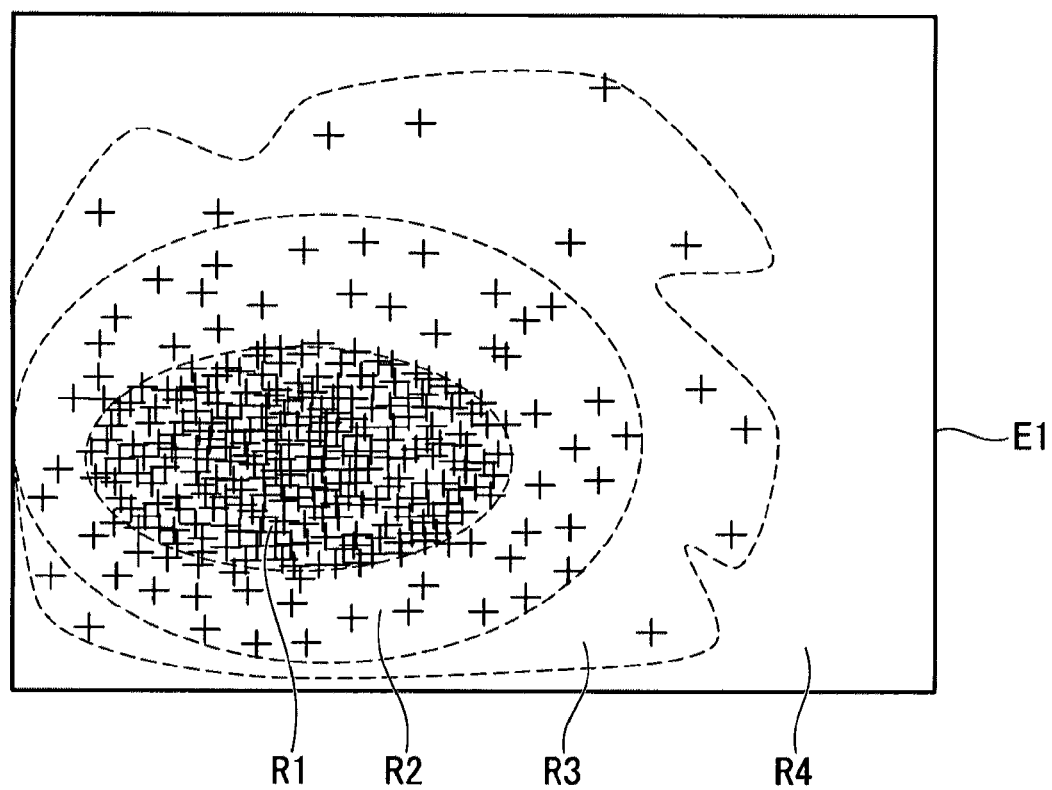
FIG. 4 is a schematic view of a first fluorescent picture image.

Here, FIG. 4 is a drawing which schematically shows a first fluorescent picture image obtained in the distribution measurement step S101. In a first fluorescent picture image E1 shown in FIG. 4, the distribution of the bright spots of fluorescence indicated by + marks in the drawing exist uneven in an observation view field E. That is, as the density with which fluorescent material exists varies by site of the sample, bright spots are numerous in portions where there are large amounts of fluorescent material, where fluorescent intensity is consequently high. On the other hand, bright spots are few in portions where there is little fluorescent material, where fluorescent intensity is accordingly low.

Such bias in fluorescent intensity is a phenomenon that is ordinarily observed in all types of samples. For example, in cell samples and the like, irregularities occur in fluorescent intensity distribution (two-dimensional luminance distribution) according to differences in density of the cell tissue. In FIG. 4, the region where bright spots are concentrated (the portion where fluorescent intensity is high) corresponds to, for example, the portion in the vicinity of the cell nucleus in a cell, and the regions where bright spots are scattered (the portions where fluorescent intensity is low) correspond to, for example, portions where organelles exist within a cell.

Figure 5:
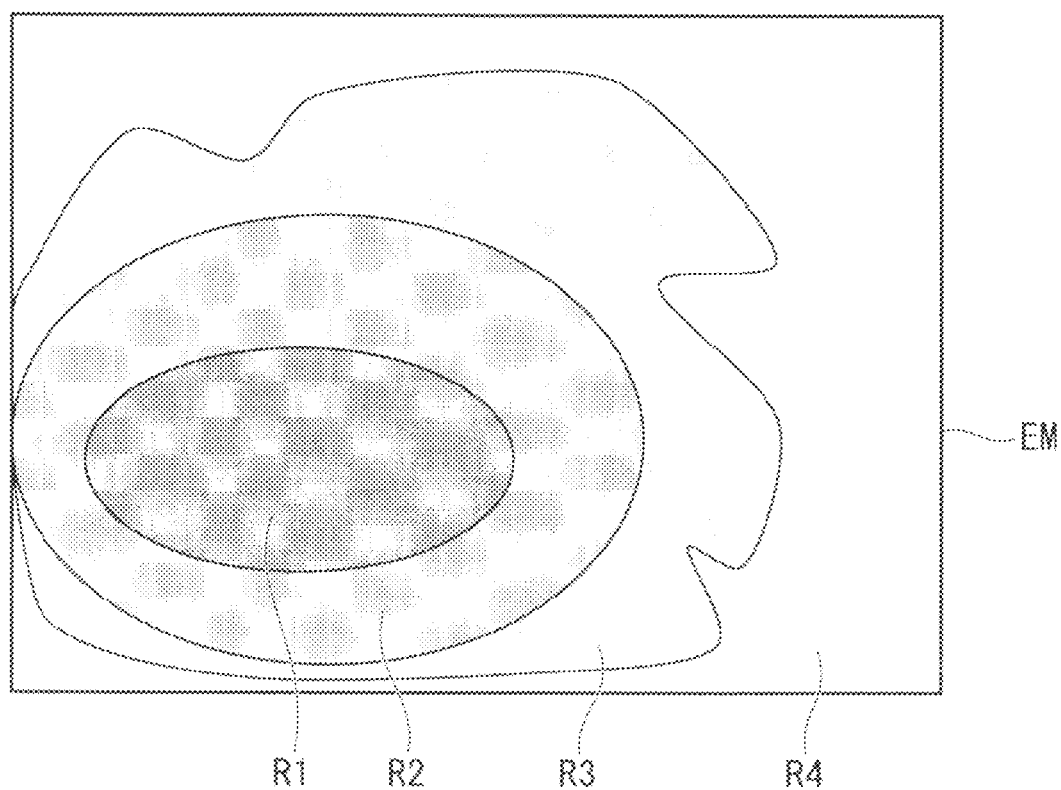
FIG. 5 is a schematic view of two-dimensional luminance distribution.

By deriving the distribution of fluorescent intensity in an observation view field from a first fluorescent picture image E1, it is possible to obtain a two-dimensional luminance distribution such as that shown, for example, in FIG. 5. A two-dimensional luminance distribution EM shown in FIG. 5 demarcates the four regions of R1-R4, and a level of fluorescent intensity is set corresponding to each region R1-R4. Region R1 corresponds to a range where bright-spot density is highest, and radiation intensity is highest. Thereafter, in the sequence of regions R2, R3, R4, there is classification according to ranges where bright-spot density decreases, and radiation intensity declines.

In FIG. 5, fluorescent intensity is classified according to four levels, but there is no particular limit on the number of classified levels. It is possible to conduct minute classification within a range that is controllable by the AOTF 42.

If the two-dimensional luminance distribution EM has been obtained according to the aforementioned procedure, transition to the irradiation intensity setting step S102 occurs, a two-dimensional intensity map is prepared, and step S13 in which storage is conducted is performed.

In step S13, the controller 14 prepares a two-dimensional intensity map which regulates the irradiation intensity of the activating light L2 at each position in the observation view field based on the two-dimensional luminance distribution EM that was calculated in the distribution measurement step S101.

With respect to preparation of the two-dimensional intensity map, the irradiation intensity of activating light L2 is set lowest relative to region R1 where fluorescent intensity is highest in the two-dimensional luminance distribution EM shown in FIG. 5, and the irradiation intensity of activating light L2 is set highest relative to region R4 where fluorescent intensity is lowest. With respect to regions R2 and R3, irradiation intensities which are intermediate between regions R1 and R4 are set according to the respective radiation intensity levels.

That is, in the observation view field, irradiation is conducted with relatively weak activating light L2 in regions R1 and R2 where large amounts of fluorescent material exist, and irradiation is conducted with relatively intense activating light L2 in regions R3 and R4 where small amounts of fluorescent material exist.

In the case of the present embodiment, as the two-dimensional intensity map is a map of control signals outputted to the AOTF controller 18, there is no particular limit on the data format, provided that the desired modulation relative to activating light L2 (variation of irradiation intensities) is possible in the AOTF 42.

With respect, for example, to the two-dimensional luminance distribution EM obtained in the distribution measurement step S101, the two-dimensional intensity map can be prepared as a map in which a reciprocal of the respective radiation intensity level is assigned to the regions R1-R4. For example, if the radiation intensity levels of the regions R1-R4 are respectively 4, 3, 2, and 1, 0.25 (¼), 0.33 (⅓), 0.5 (½), and 1 (1/1) are respectively set as control values of irradiation intensity with respect to the regions R1-R4 in the two-dimensional intensity map.

Or one may prepare the two-dimensional luminance distribution EM as a reverse image which has undergone tonal inversion. For example, when tonal values corresponding to the radiation intensity levels of the regions R1-R4 are 200, 150, 100, and 50, and when the range of tonal values is 1-255, one respectively sets 55, 105, 155, and 205 as the control values of irradiation intensity in the regions R1-R4 of the two-dimensional intensity map.

The two-dimensional intensity map (irradiation intensity distribution data) that is generated in the irradiation intensity setting step S102 in this manner is stored in the memory 16 from the controller 14.

When setting of the two-dimensional intensity map terminates, the controller 14 initiates the picture image formation step S103. In the picture image formation step S103, STORM photographic processing (steps S14-S17) which obtains from several hundred to several tens of thousands of second fluorescent picture images using the two-dimensional intensity map that was set in the irradiation intensity setting step S102, and STORM picture image processing (step S18) which generates a sample picture image from the second fluorescent picture images are performed.

First, in step S14, the sample is irradiated with controlled activating light L2. In the microscope apparatus 10, the shutter 22 of the excitation illumination system 11 is closed, and only activating light L2 is supplied to the microscope body 15. The controller 14 reads out the two-dimensional intensity map that is stored in the memory 16, and the individual pieces of data (control signals) that configure the two-dimensional intensity map are transmitted to the AOTF controller 18. The AOTF controller 18 drives the AOTF 42 based on the inputted control signals.

In the activation illumination system 13, the activating light L2 emitted from the laser light source 41 is modulated to the irradiation intensities which were set in the two-dimensional intensity map by the AOTF 42 that is driven by the AOTF controller 18. The activating light L2 of controlled irradiation intensity is position-controlled by the scanner 43, is received by the dichroic mirror 33, is reflected by the dichroic mirror 33, and is irradiated onto the prescribed position of the observation view field on the stage 31.

At this time, in the case where the microscope apparatus 10 is in the total reflection illumination mode, the activating light L2 irradiates the sample S as evanescent light EV, selectively activating only the fluorescent material that is positioned on the actual surface layer portion of the sample S, as shown in FIG. 3.

In the aforementioned step S14, as irradiation occurs with activating light L2 whose irradiation intensities are controlled by portion of the observation view field based on the two-dimensional intensity map, irradiation occurs with activating light L2 of relatively low intensity in regions where the fluorescent material within the observation view field exists at relatively high density (high-density regions), and irradiation occurs with activating light L2 of relatively high intensity in regions where the fluorescent material exists at relatively low density (low-density regions).

When this is done, the probability that the fluorescent material has been activated in the aforementioned high-density region is relatively low, and the probability that fluorescent material has been activated in the low-density region is relatively high. However, on the other hand, as the amount of fluorescent material in the high-density region is large, and as the amount of fluorescent material in the low-density region is small, the amount of fluorescent material that is activated by the activating light L2 is approximately the same amount in the high-density region and the low-density region.

Next, when transition to step S15 occurs, the activation illumination system 13 enters a state where activating light L2 is not emitted, the shutter 22 of the excitation illumination system 11 is opened, and exciting light L1 emitted from the laser light source 21 is supplied to the microscope body 15 via the total reflection mirror 32. As a result, the entire observation view field is irradiated with exciting light L1, and selective light emission occurs only with respect to fluorescent material that has been activated by the activating light L2. The fluorescent material that has emitted fluorescence transitions to an inactive state. The fluorescence emitted by this fluorescent material is photographed by operating the camera 34 via the camera controller 19, enabling obtainment of a second fluorescent picture image. The photographed second fluorescent picture image is sent to the controller 14 from the camera controller 19.

Figure 6:
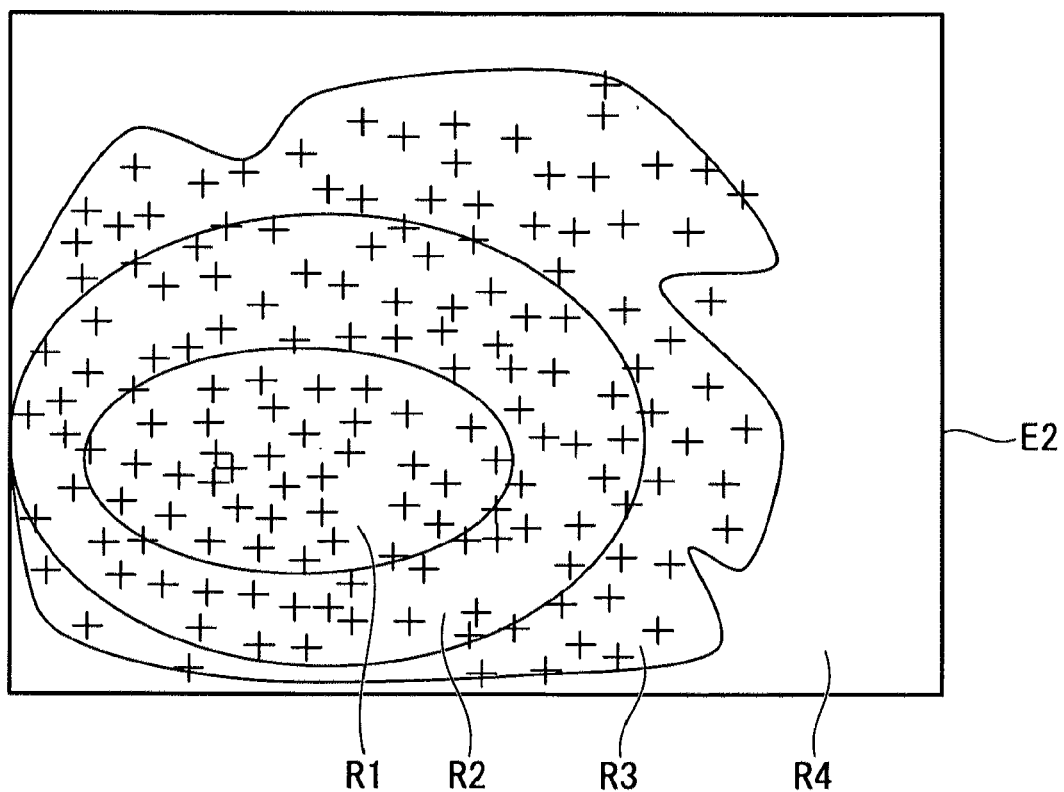
FIG. 6 is a schematic view of a second fluorescent picture image.

Here, FIG. 6 is a drawing which schematically shows a second fluorescent picture image. In a second fluorescent picture image E2 shown in FIG. 6, the bright spots of fluorescence that have been photographed are indicated by + marks, and the densities of bright spots in the respective regions R1-R4 can be identified by superimposed illustration of the boundaries of the regions R1-R4 in the two-dimensional luminance distribution EM. As shown in FIG. 6, with respect to the second fluorescent picture image E2 obtained in the present embodiment, the density of bright spots (+ marks) in each region R1-R3 has been made approximately uniform. This is because correction has been conducted to render the amounts of activated fluorescent material in the regions R1-R3 approximately identical by lowering the irradiation intensity of activating light L2 relative to region R1, and by raising the irradiation intensity of activating light L2 relative to region R3.

In step S16, the controller 14 stores the second fluorescent picture image that is received in the memory 16. When the second florescent picture image is stored in the memory 16, it is determined in step S17 whether or not STORM photographic processing has terminated. That is, it is determined whether or not obtainment of the preset number of second fluorescent picture images has terminated. In the case where the number of second fluorescent picture images has not reached the planned number, return to step S14 ensues, and the above-described steps S14-S16 are repeated.

In the case of the present embodiment, the fluorescent material that has emitted light in step S15 has become inactive upon light emission, and consequently in the case where a return from step S17 to step S14 occurs, and where irradiation with activating light L2 is again conducted, the fluorescent material contained in the sample S is in an inactive state. Consequently, each time that step S14 is repeated, the activated fluorescent material stochastically differs, and the second fluorescent picture image that is subsequently obtained in step S15 will exhibit a bright-spot pattern which is different from that of the second fluorescent picture image obtained in the preceding cycle.

In this manner, by repetitively performing steps S14-S16, from several hundred to several tens of thousands of second fluorescent picture images with different bright spot positions will be obtained.

Obtainment of second fluorescent picture images from several hundred to several tens of thousands of times in this manner is possible, because the fluorescent material imparted to the sample S has the property of returning to an inactive state when light emission is induced, the light emission time per image pickup can be shortened, the period until color fading can be lengthened, the fluorescent material that is activated by activating light L2 is only a small portion of the whole, and the fluorescent material that emits light at a single image pickup is a comparatively small amount.

On the other hand, in the case where pickup of the planned number of second fluorescent picture images is completed, it is determined in step S17 that termination has occurred, and transition to step S18 ensues.

In step S18, a sample picture image is generated by superimposing the several hundred to several tens of thousands of second fluorescent picture images that have accumulated in the memory 16. When the second fluorescent picture images are superimposed, the multiple fluorescent bright spots existing at a coordinate that is considered to be approximately identical among the multiple second fluorescent picture images are converted into a single fluorescent bright spot.

As the irradiation intensity of activating light L2 is varied by region in the present embodiment, the probability that fluorescent material will be activated differs by region. Particularly in region R3 where the density of fluorescent material is comparatively low, when the irradiation intensity of activating light L2 is raised, the probability of activation of the same fluorescent material rises. By culling the fluorescent bright spots that are considered to be identical in the aforementioned manner, it is possible to prevent occurrence of flaws in the sample picture image deriving from the variation of irradiation intensity Fluorescent bright spots that are considered to be identical can be evaluated according to their interstices. For example, one can establish settings so that it is determined that fluorescent bright spots are identical in cases where the interstices are less than STORM resolution (approximately 20 nm).

Or, instead of the above-described method which culls fluorescent bright spots, one may adopt a method which generates an information-added picture image by adding information of a two-dimensional intensity map to a generated sample picture image. That is, it is also acceptable to prepare a sample picture image by superimposing second fluorescent picture images as is, and perform coloration with colors that differ according to the respective regions R1-R4 with respect to the prepared sample picture image. When this is done, it is possible to prevent distortion of the picture image in the region R1 where the density of fluorescent material is comparatively high, and enhance the color definition of the picture image in the region R3 where density is comparatively low. On the other hand, as the sample picture image is such that the fluorescent material appears to be uniformly distributed, it is possible to offer information based on the density of fluorescent material to the user by adding the information of a two-dimensional intensity map by color-coding the regions R1-R4 where irradiation intensity varies, and conducting display or the like.

Otherwise, as information corresponding to the irradiation intensity of activating light L2, in addition to the aforementioned color coding, one may also use a method wherein the boundary lines of the regions R1-R4 are shown by superimposition in the sample picture image, a method wherein background colors of the sample picture image are varied according to the regions R1-R4, and so on.

According to the observation method of the present embodiment described above, it is possible to attain a clear sample picture image even when the density of the fluorescent material in the observation view field is uneven. The pertinent operational effects are described in detail below.

Figure 7A:
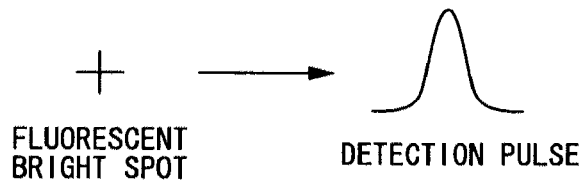
FIG. 7A is an explanatory view pertaining to detection of a fluorescent bright spot.
Figure 7B:
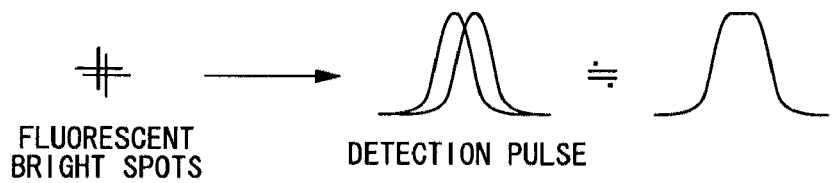
FIG. 7B is an explanatory view pertaining to detection of fluorescent bright spots.
Figure 7C:
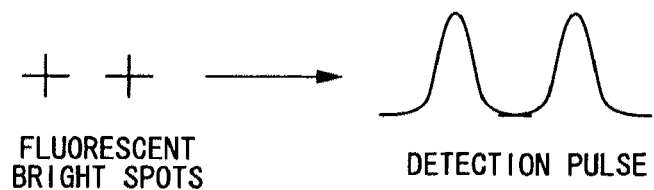
FIG. 7C is an explanatory view pertaining to detection of fluorescent bright spots.

With conventional STORM photographic processing, in the case where there is bias in the fluorescent material as in the first fluorescent picture image E1 shown in FIG. 4, the picture image would be distorted in regions where fluorescent material is tightly packed such as region R1. As shown in FIG. 7B, this is because when two fluorescent bright spots are arranged in close proximity, the detection pulses inseparably overlap, and it becomes impossible to detect them as two fluorescent bright spots. To detect fluorescent bright spots for each molecule of fluorescent material, it would be necessary to have a single molecule of fluorescent material in isolation, or to arrange the molecules of fluorescent material with appropriate separation, as shown in FIG. 7A and FIG. 7C.

In the observation method of the present embodiment, the irradiation intensity of activating light L2 is varied according to the density of fluorescent material in the observation view field. That is, irradiation is conducted with relatively weak activating light L2 in regions where relatively large amounts of fluorescent material exist, and irradiation is conducted with relatively strong activating light L2 in regions where relatively small amounts of fluorescent material exist. As a result, it is possible to make the density of the fluorescent bright spots (+ marks) in regions R1-R3 approximately uniform as shown in FIG. 6, and to properly separate fluorescent bright spots as shown in FIG. 7C. Thus, according to detection of fluorescent bright spots based on FIG. 6, it is possible to identify fluorescent bright spots corresponding to single molecules of fluorescent material.

Otherwise, the average interstice between fluorescent bright spots in FIG. 6 can be adjusted according to the irradiation intensity of activating light L2. If the irradiation intensity of the activating light L2 is raised, a greater amount of fluorescent material is activated, with the result that the average interstice between fluorescent bright spots is narrowed. Conversely, the interstice is widened when irradiation intensity is lowered.

When the interstice between fluorescent bright spots is excessively narrow, it is difficult to detect the individual fluorescent bright spots, as shown in FIG. 7B. On the other hand, as the number of fluorescent bright spots in a single second fluorescent picture image decreases when the interstice is excessively wide, the number of required second fluorescent picture images increases, measurement time is lengthened, and color fading of the fluorescent material tends to become problematic.

Accordingly, it is preferable that the irradiation intensity of activating light L2 be adjusted so that the average interstice between fluorescent bright spots (density of fluorescent bright spots) is in an appropriate range. Specifically, it is preferable that the interstice between fluorescent bright spots in a second fluorescent picture image be set at double or more the optical resolution of the microscope apparatus 10, and triple is more preferable. Individual fluorescent bright spots can be identified if the interstice is at least double or more the optical resolution. If set at triple the optical resolution, observation can be efficiently conducted, as the fluorescent bright spots can be arranged at comparatively high density.

For example, if the optical resolution of the microscope apparatus 10 is 200 nm, one may adjust the irradiation intensity of activating light L2 so that the average interstice between fluorescent bright spots in a second fluorescent picture image is on the order of 600 nm. Specifically, with respect to a two-dimensional intensity map, one may increase or decrease the control values of the entire two-dimensional intensity map while maintaining the differential or ratio of control values by region.

In order to adjust the aforementioned interstice between fluorescent bright spots, one may readjust the irradiation intensity of activating light L2 based on a second fluorescent picture image obtained in step S15. In this case, the controller 14 analyzes the second fluorescent picture image obtained from the camera controller 19, and computes an average interstice between fluorescent bright spots. In the case where the computed interstice is less than double the optical resolution, the irradiation intensity of activating light L2 with which irradiation is to be conducted in the step S14 that is to be performed next is corrected downward. Or, in the case where the computed interstice is excessively wide at, for example, four times or more the optical resolution, the irradiation intensity of activating light L2 is corrected upward.

Furthermore, in the case where an average interstice between fluorescent bright spots is computed from a second fluorescent picture image after the aforementioned correction, and the computed interstice exceeds the appropriate range, correction of the aforementioned irradiation intensity of activating light L2 may be performed again. Moreover, it is also acceptable to repeat correction of the irradiation intensity of activating light L2 until the average interstice between fluorescent bright spots is in the appropriate range (at least double or more the optical resolution).

In the present embodiment, after conducting irradiation with the activating light L2 in step S14, operations for obtainment of second fluorescent picture images may be repetitively performed for several times in steps S15 and S16. By this means, second fluorescent picture images can be efficiently obtained by effectively utilizing activated fluorescent material.

As fluorescent material that emits light becomes inactive, the number of fluorescent bright spots that are observed gradually decreases when irradiation with exciting light L1 is repeated in this manner. As the time for obtainment of second fluorescent picture images is unnecessarily lengthened when the number of bright spots is too few, the number of repetitions of step S15 is on the order of 2-5 times.

In the case where irradiation with exciting light is conducted multiple times relative to a single instance of the aforementioned activating light irradiation, adjustment of the average interstice of bright spots (adjustment of the irradiation intensity of activating light L2) is conducted based on the second fluorescent picture image obtained by the initial exciting light irradiation. This is because detection of individual bright spots is facilitated, given that the number of bright spots decreases and the average interstice increases in second fluorescent picture images from the second time onward.

By adjusting the irradiation intensity of activating light L2 based on the information of second fluorescent picture images in the aforementioned manner, and by adjusting the interstice between bright spots to an appropriate range in second fluorescent picture images obtained in cycles from the next time onward, it is possible to efficiently obtain picture images of high resolution.

In the present embodiment, a first fluorescent picture image may also be used as a portion of a second fluorescent picture image. As a first fluorescent picture image also picks up the fluorescent bright spots of the fluorescent material of the sample, it may be used to prepare a sample picture image by superimposition together with a second fluorescent picture image. When the intensity of the activating light L2 is adjusted so that regions do not occur where fluorescent bright spots are excessively concentrated in a first fluorescent picture image, a first fluorescent picture image can be made which can be suitably used in superimposition for a sample picture image.

Moreover, in the present embodiment, multiple first fluorescent picture images may be obtained for preparation of a two-dimensional intensity map. In this case, the sample may be irradiated with activating light L2 each time that a first fluorescent picture image is obtained, and operations for obtainment of a first fluorescent picture image may be performed multiple times after a single instance of irradiation with activating light L2.

When a two-dimensional intensity map is prepared, a two-dimensional luminance distribution is computed with respect to a picture image in which a plurality of obtained first fluorescent picture images is superimposed.

By using multiple first fluorescent picture images to prepare a two-dimensional intensity map, the number of fluorescent bright spots can be reduced in the individual first fluorescent picture images, thereby facilitating obtainment of first fluorescent picture images that can be used as part of a sample picture image.

Second Embodiment

Figure 8:
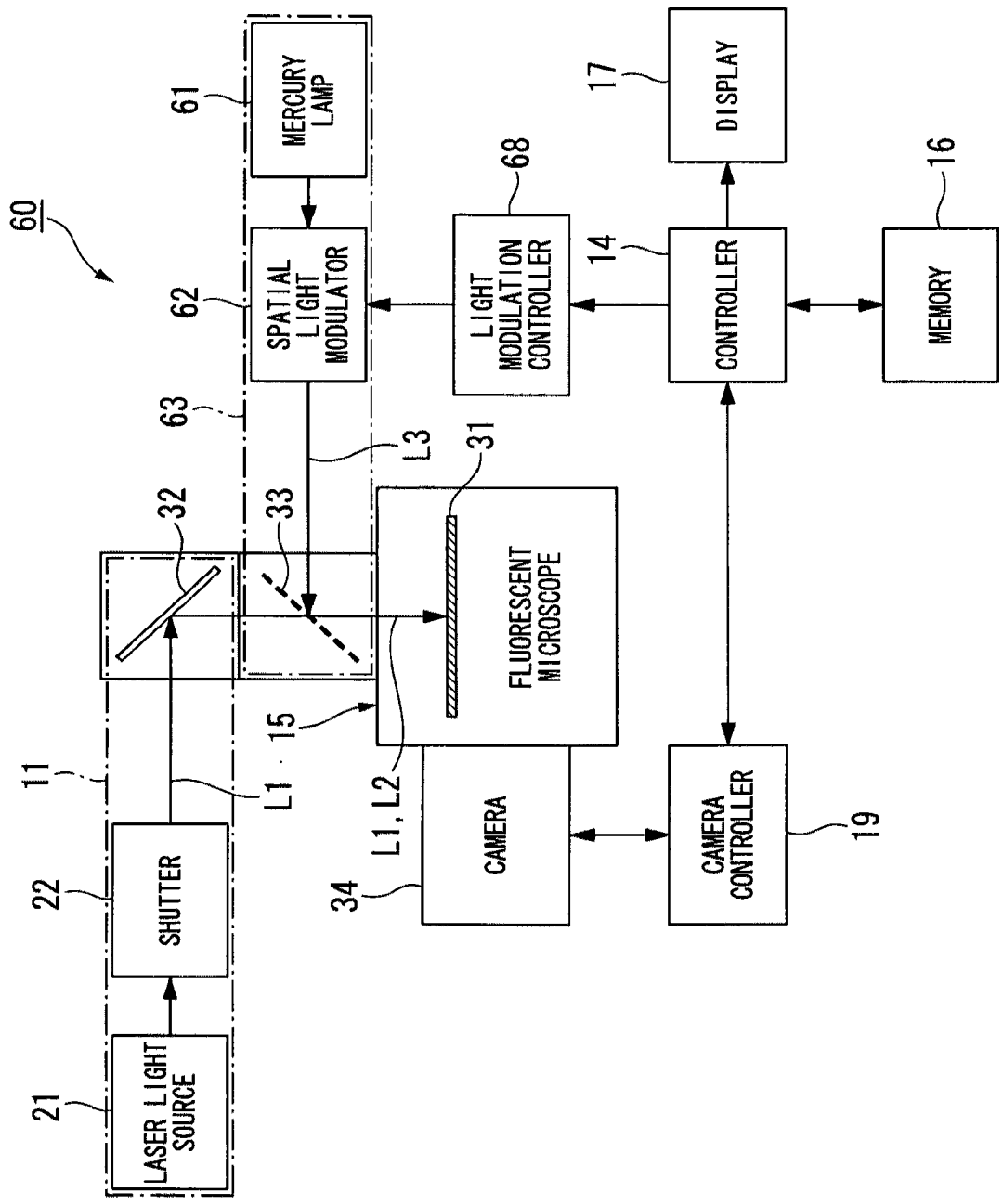
FIG. 8 is a block diagram which shows a second embodiment the microscope apparatus.

FIG. 8 is a schematic view which shows the microscope apparatus of a second embodiment. Components that are common to the first embodiment are assigned the same reference numbers in FIG. 8, and detailed description thereof is omitted.

A microscope apparatus 60 of the second embodiment is configured so as to be provided with an activation illumination system 63, instead of the activation illumination system 13 of the first embodiment. The activation illumination system 63 is provided with a mercury lamp 61, a spatial light modulator 62, and the dichroic mirror 33, and is connected to the microscope body 15 via the dichroic mirror 33. The spatial light modulator 62 is connected to a light modulation controller 68, and the light modulation controller 68 is connected to the controller 14.

The spatial light modulator 62 is, for example, a DMD (Digital Mirror Device; registered trademark) or a liquid crystal panel. A DMD is provided with a configuration wherein numerous micromirrors are planarly arranged. In the case where a DMD is used as the spatial light modulator 62, the micromirror angles are switched at high speed and the direction of reflection of incident light is controlled based on drive signals inputted from the light modulation controller 68, thereby enabling control of the amount of light emitted in the regions corresponding to the individual micromirrors.

As a result, the activation illumination system 63 modulates the activating light L3 that is emitted from the mercury lamp 61 by the spatial light modulator 62, and enables supply thereof to the microscope body 15 as surface illumination having the desired irradiation intensity distribution.

In the microscope apparatus 60 of the second embodiment, the spatial light modulator 62 is used as the apparatus which modulates the activating light L2, thereby enabling irradiation of the observation view field with activating light L2 whose irradiation intensity is controlled by region as in the first embodiment. Accordingly, it is possible to implement the same observation method as the first embodiment.

Otherwise, with the activation illumination system 63 of the second embodiment, there is no need to provide a scanner for scanning laser light as in the activation illumination system 13 of the first embodiment.

Third Embodiment

In the foregoing embodiments, the descriptions concerned a microscope apparatus which uses two lasers with different wavelengths for activation and excitation. On the other hand, dSTORM (direct Stochastic Optical Reconstruction Microscopy) is known as a super-resolution microscope technology that uses only a single short-wavelength laser (e.g., paper: Applied Physics B (2008)93: 725-731, Photoswitching Microscopy with Standard Fluorophores, S. van de Linde, R. Kasper, M. Heilemann, M. Sauer). With respect to dSTORM, there is no irradiation with an activation-use laser as in conventional STORM, and a picture image with only a small number of fluorochromes is obtained based on spontaneous flickering of the fluorescent material.

The fluorescent microscope apparatus of the third embodiment is configured to apply this dSTORM.

As the microscope apparatus of the third embodiment, one may adopt a configuration which omits the activation illumination system 13 from the microscope apparatus 10 shown in FIG. 1 With the microscope apparatus of the pertinent configuration, a sample which comprises fluorescent material that spontaneously flickers when irradiated by the excitation illumination system 11 with exciting light of a prescribed wavelength is arranged in an observation region on the stage 31 of the microscope body 15, flickering of the fluorescent material is caused by irradiation of this observation region with exciting light from the excitation illumination system 11, and a fluorescent picture image is obtained by using the camera 34 to photograph the light that radiates from the fluorescent material.

In the microscope apparatus of the third embodiment, the controller 14 measures the fluorescent intensity distribution of the observation region based on signals from the camera controller 19, and sets the irradiation intensity of exciting light by portion of the observation region based on the fluorescent intensity distribution. The controller 14 alternately and multiply repeats an operation in which the observation region is irradiated with exciting light of an irradiation intensity that is set by portion, and an operation in which a fluorescent picture image excited by the exciting light of the observation region is obtained, whereby multiple fluorescent picture images are obtained, and a sample picture image is generated from the multiple fluorescent picture images.

Accordingly, the procedure of the observation method of the third embodiment has a distribution measurement step 101, an irradiation intensity setting step S102, and a picture image formation step S103, as in the observation method of the first embodiment shown in FIG. 1. However, in the case of the present embodiment, with respect to the distribution measurement step S101, the excitation illumination system 11 is used, rather than the activation illumination system 13.

In the present embodiment, with respect to the distribution measurement step S101, the observation region is irradiated with exciting light L1 of uniform intensity distribution from the excitation illumination system 11. The fluorescence which is emitted from the fluorescent material that is irradiated with the exciting light L1 is photographed by operating the camera 34 via the camera controller 19. The photographed first fluorescent picture image is transmitted to the controller 14 from the camera controller 19. The controller 14 computes a two-dimensional luminance distribution (fluorescent intensity distribution) in the first fluorescent picture image.

Subsequently, in the irradiation intensity setting step S102, a two-dimensional intensity map is prepared from the two-dimensional intensity distribution, as in the first embodiment.

On the other hand, in the picture image formation step S103, the sample is irradiated with exciting light L1 while modulating irradiation intensity based on the two-dimensional intensity map prepared in the irradiation intensity setting step S102, whereby from several hundred to several tens of thousands of second fluorescent picture images are obtained, and a sample picture image is generated from the second fluorescent picture images. The intensity of activating light L2 was modulated in the first embodiment, but in the present embodiment, fluorescent material emits light by irradiation with exciting light L1 alone, and irradiation is consequently conducted while modulating the intensity of exciting light L1.

According to the third embodiment described above, a picture image of high resolution can be obtained even in cases where large bias exists in the distribution of fluorescent material, as in the preceding embodiments. Moreover, as fluorescent material is used which spontaneously flickers due to the emission of exciting light, the illumination system can be simplified.

Fourth Embodiment

In the foregoing first embodiment, the description concerned microscopy (STORM) which uses fluorescent material that becomes inactive by emitting fluorescence when irradiated with exciting light after activation, but PALM (Photoactivated Localization Microscopy) is also known as a similar technology with a different type of fluorescent material (e.g., Published Japanese Translation of PCT Application No. 2008-542826; paper: Proposed Method for Molecular Optical Imaging, Optics Letters, vol. 20, No. 3, (Feb. 1, 1995), pp. 237-239).

The procedure of the observation method of the foregoing first embodiment is applied without alteration even in the case where PALM is used to obtain a sample picture image, and it is also not necessary to modify the configuration of the microscope apparatus 10, 60. In the microscope apparatus 10 or the microscope apparatus 60, the controller 14 measures the fluorescent intensity distribution of the observation region based on signals from the camera controller 19, and sets the irradiation intensity of exciting light for each portion of the observation region based on the fluorescent intensity distribution. The controller 14 obtains multiple fluorescent picture images by alternately and multiply repeating an operation in which the observation region is irradiated with activating light at the irradiation intensities set for each portion, and an operation in which a fluorescent picture image is obtained by conducting irradiation with exciting light; it then generates a sample picture image from the multiple fluorescent picture images.

In the case where PALM is used, the fluorescent material imparted to the sample is changed. Specifically, as the fluorescent material, fluorescent material is used which is activated when irradiated with activating light of a prescribed wavelength, and which emits fluorescence when irradiated in an activated condition with exciting light of a wavelength that differs from that of the activating light.

As this type of fluorescent material, one may cite variable species of fluorescent proteins derived from medusa or coral. For example, with respect to PA-GFP, which is a variable species of fluorescent protein derived from medusa, fluorescent intensity is greatly increased due to irradiation with activating light, while PS-CFP is changed by irradiation with activating light to enable emission of fluorescent light of other colors. Dronpa, which is a variable species of fluorescent protein derived from coral, becomes capable of light emission by irradiation with light of an excitation wavelength as a result of irradiation with activating light, and Kaede undergoes a change in fluorescent color due to irradiation with activating light.

In the observation method of the present embodiment, a sample picture image of high resolution can be obtained by sequentially forming the distribution measurement step S101, irradiation intensity setting step S102, and picture image formation step S103 shown in FIG. 2.

In step S11 of the distribution measurement step S101, after the sample is irradiated with activating light L2 of uniform intensity from the activation illumination system 13, the sample is irradiated with exciting light L1, and a first fluorescent picture image is obtained by observation of the emitted light. In the case of the present embodiment, as well, the first fluorescent picture image E1 shown in FIG. 4 is, for example, obtained.

Otherwise, in the case where fluorescent protein (PS-CFP or Kaede) is used which emits light due to irradiation with exciting light even in a state where irradiation with activating light has not been conducted, irradiation with activating light in the distribution measurement step S101 is unnecessary, as it is sufficient if the fluorescent light prior to change (blue light of PS-CFP or green light of Kaede) is observed.

In the case where fluorescent material which is capable of becoming inactive is used, after performance of the distribution measurement step S101, one may render the fluorescent material inactive to inhibit the progression of fading of the fluorescent material. For example, in the case where kindling fluorescent protein is used, it is sufficient if the irradiation intensity of the irradiating activating light in the distribution measurement step S101 is set at an irradiation intensity that produces spontaneous deactivation in the fluorescent material. In addition, one may also use a fluorescent protein such as Dronpa that is returned to an inactive state by continuous irradiation with exciting light Next, in step S12, a two-dimensional intensity distribution is computed in a first fluorescent picture image. The specific processing of the pertinent step is identical to that of the first embodiment, and results in obtainment of the two-dimensional luminance distribution EM shown in FIG. 5.

Next, in the irradiation intensity setting step S102, a two-dimensional map of the irradiation intensity of activating light L2 is prepared based on the two-dimensional luminance distribution EM. The specific processing of the pertinent step is identical to that of the first embodiment, and the prepared two-dimensional intensity map is stored in the memory 16.

Next, in step S14 of the picture image formation step S103, the sample is irradiated with activating light L2 that is modified using the two-dimensional intensity map prepared in the aforementioned manner. That is, based on the two-dimensional intensity map, regions where fluorescent material exists in high density are irradiated with activating light L2 of relatively low intensity, while regions where fluorescent material exists in low density are irradiated with activating light L2 of relatively high intensity. As a result, the density of activated fluorescent material is leveled across the entire view field.

Next, in step S15, the sample is irradiated with exciting light L1. As a result, the fluorescent material in an activated state emits light, the emitted light is picked up by the camera 34, and a second fluorescent picture image is obtained. In the case of the present embodiment, as in the first embodiment, a second fluorescent picture image is obtained in which fluorescent bright spots exist with approximately uniform density, as in the second fluorescent picture image E2 shown in FIG. 6. The obtained second fluorescent picture image is stored in the memory 16 in step S16.

In the case of the present embodiment, the operations for obtainment of second fluorescent picture images in step S15 and S16 are repetitively performed until the fluorescent material activated in step S14 either has faded or is returned to an inactive state.

Next, in step S17, the termination of image pickup is assessed. In the case where image pickup has not terminated, a return to step S14 occurs, and the operations that irradiate the sample with activating light L2 are performed. As a result of irradiation with this activating light L2, fluorescent material that has not faded is activated. Subsequently, the operations of step S15 and S16 that obtain and store a second fluorescent picture image are performed When the operations from step S14 to step S16 are repetitively performed the number of times that has been set in advance, and it is determined in step S17 that image pickup has terminated, transition to step S18 occurs. A sample picture image of high resolution is then prepared from the numerous second fluorescent picture images by performing the picture image processing operations of step S18.

According to the fourth embodiment described above, as in the foregoing embodiments, a picture image of high resolution can be obtained even in the case of large bias in the distribution of the fluorescent material.

Fifth Embodiment

Figure 9:
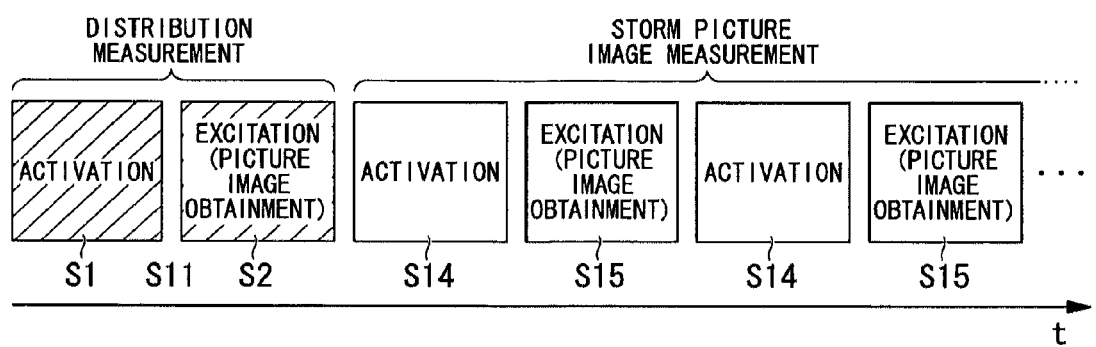
FIG. 9 is a drawing which shows a first aspect of the observation method that is referenced in a fifth embodiment.
Figure 10:
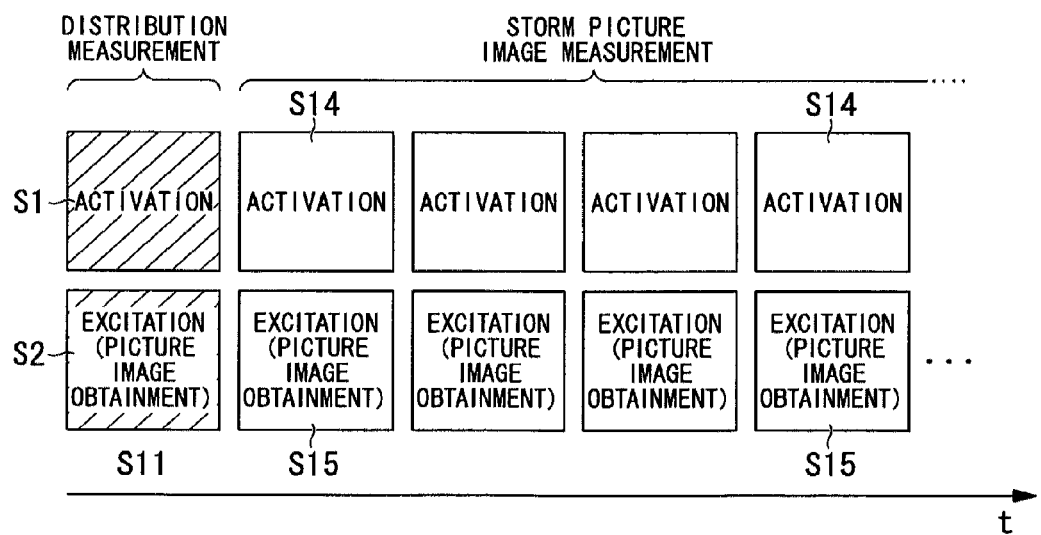
FIG. 10 is a drawing which shows a second aspect of the observation method that is referenced in the fifth embodiment.
Figure 11:
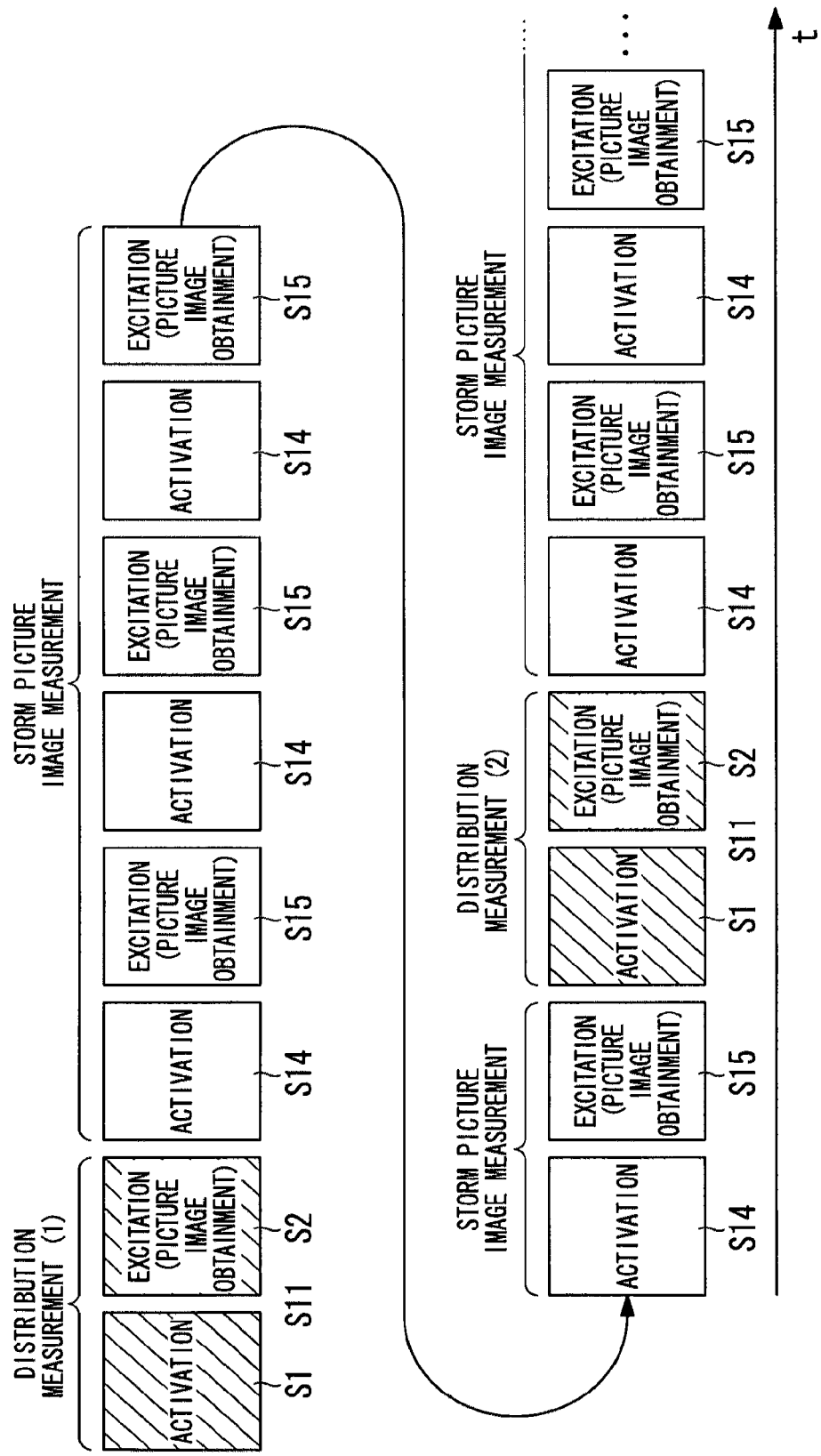
FIG. 11 is a drawing which shows a third aspect of the observation method that is referenced in the fifth embodiment.

FIG. 9 to FIG. 11 are explanatory views of the observation method of a fifth embodiment. FIG. 9 is a drawing which shows the observation method used in the preceding embodiments (first aspect). FIG. 10 is a drawing which shows a second aspect of the observation method. FIG. 11 is a drawing which shows a third aspect of the observation method. The observation method of the second aspect can be applied to the above-described first, second, and fourth embodiments, while the observation method of the third aspect can be applied to any of the preceding first through fourth embodiments.

Otherwise, in FIG. 9 to FIG. 11, among the respective steps shown in FIG. 2, only the steps requiring description are displayed and described. Specifically, illustration is omitted with respect to step S12 in which a two-dimensional luminance distribution is calculated, step S13 in which a two-dimensional intensity map is prepared, step S16 in which a second fluorescent picture image is stored, and so on.

With the observation method of the first aspect in the microscope apparatuses of the aforementioned first, second, and fourth embodiments, with respect to step S11 in which a first fluorescent picture image is obtained in order to measure distribution of the fluorescent material, as shown in FIG. 9, step S1 is first performed in which the sample is irradiated with activating light L2, and the fluorescent material contained in the sample is activated. Subsequently, step S2 is performed in which the sample is irradiated with exciting light L1, light emitted from the sample is detected, and a first fluorescent picture image is obtained.

In STORM (PALM) photographic processing, a step S14 in which a sample is irradiated with activating light L2 whose irradiation intensity is controlled based on a two-dimensional intensity map, and in which fluorescent material is activated, and a step S15 in which irradiation is conducted with exciting light L1 to cause light emission of the fluorescent material, and in which a second fluorescent picture image is obtained are repetitively performed in this sequence until the prescribed number of second fluorescent picture images is obtained.

In contrast to the foregoing, in the second aspect shown in FIG. 10, with respect to step S11 in which a first fluorescent picture image is obtained in order to measure distribution of the fluorescent material, there is simultaneous performance of a step S1 in which a sample is irradiated with activating light L2, and a step S2 in which a first fluorescent picture image is obtained by irradiating the sample with exciting light L1. In this instance, there is no need to match the start timing and end timing of step S1 and step S2, and it is sufficient if there is at least a period of simultaneous performance.

By simultaneously performing steps S1 and S2 in the foregoing manner, it is possible to cause light emission of fluorescent material by advancing approximately simultaneously with activation and excitation of the fluorescent material. Accordingly, as in the first aspect, the observation method of the second aspect enables obtainment of a first fluorescent picture image, and enables obtainment of a fluorescent intensity distribution.

Moreover, with respect to the second aspect shown in FIG. 10, in STORM (PALM) photographic processing as well, there is simultaneous performance of a step S14 in which a sample is irradiated with activating light L2, and a step S15 which a second fluorescent picture image is obtained by irradiating the sample with exciting light L1. In this instance, as well, there is no need to match the start timing and end timing of step S14 and step S15, and it is sufficient if there is at least a period of simultaneous performance.

By simultaneously performing steps S14 and S15, it is possible to cause light emission of fluorescent material by advancing approximately simultaneously with activation and excitation of the fluorescent material, thereby enabling obtainment of a second fluorescent picture image as in the first aspect.

In the case where exciting light irradiation and picture image obtainment are conducted multiple times with respect to a single activating light irradiation, it is sufficient if irradiation with the exciting light L1 is conducted at least once during the period in which the sample is being irradiated with the activating light L2. For example, in the case where irradiation with the exciting light L1 is conducted three times, it is sufficient if the initial irradiation period of the exciting light L1 is set in a simultaneous irradiation period of the activating light L2, and it is also acceptable to conduct irradiation with the exciting light L1 twice during the irradiation period of the activating light L2.

According to the observation method of the aforementioned second aspect, activation and excitation of the fluorescent material are simultaneously performed.

As a result, it is possible to shorten the time required for picture image obtainment compared to the preceding first aspect, and to efficiently measure and prepare a high-resolution picture image.

Next, in the foregoing first to the fourth embodiments, a distribution measurement step S101 for obtainment of the distribution of fluorescent material, and an irradiation intensity setting step S102 for preparation of a two-dimensional intensity map that serves to control the irradiation intensities of activating light L2 are respectively conducted only once, as shown in FIG. 2.

In contrast to this, with the observation method of a third aspect shown in FIG. 11, a step S11 (steps S1 and S2) which obtains a first fluorescent picture image is initially conducted, after which there is multiple performance (4 times in the drawing) of a step S14 in which irradiation is conducted with activating light L2 that is modulated based on the two-dimensional intensity map prepared based on the first fluorescent picture image, and a step S15 in which a second fluorescent picture image is obtained by conducting irradiation with exciting light L1.

After obtainment of the prescribed number of second fluorescent picture images, step S11 (steps S1 and S2) which obtains a first fluorescent picture image is again performed, and the two-dimensional intensity map is updated by computation based on the pertinent first fluorescent picture image.

Subsequently, step S14 in which irradiation is conducted with activating light L2 that is modulated based on the updated two-dimensional intensity map, and step S15 in which a second fluorescent picture image is obtained by conducting irradiation with exciting light L1 are performed the prescribed number of times. The operations which update the two-dimensional intensity map are performed as necessary.

In the third aspect, the interval for the updating operations of the two-dimensional intensity map may be set as desired. The updating operations of the two-dimensional intensity map may be set to at least one time for the period in which the prescribed number of second fluorescent picture images is obtained, and may be set so as to be performed whenever the prescribed number (e.g., 100, 500, 1000 or the like) of second fluorescent picture images is obtained.

In the third aspect shown in FIG. 11, as a two-dimensional intensity map is updated during the operations which obtain from several hundred to several tens of thousands of second fluorescent picture images, the activating light L2 is modulated using the two-dimensional intensity map according to the color fading condition of the fluorescent material in conjunction with the progress of STORM (PALM) photographic processing. This results in an observation method which enables efficient obtainment of second fluorescent picture images that contain the appropriate number of fluorescent bright spots.

Sixth Embodiment

Figure 12:
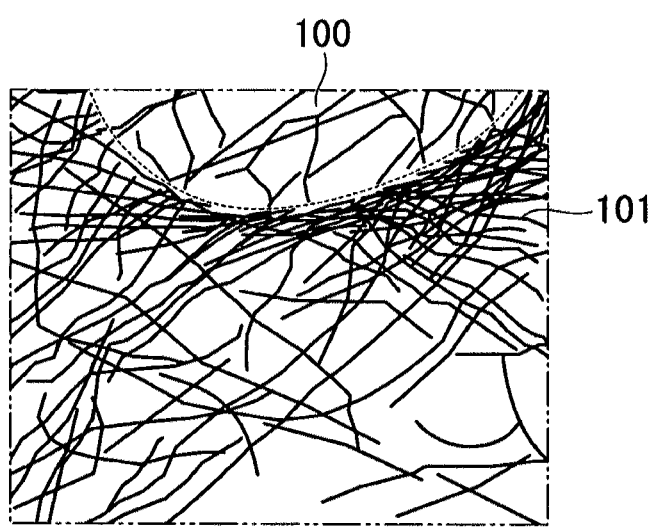
FIG. 12 is a drawing which shows a cell observation picture image that is referenced in a sixth embodiment.

According to the microscope apparatus of each of the foregoing embodiments, it is not only possible to conduct fixed sample observation, but also, for example, live cell observation like that shown in FIG. 12. Below, description is given of a case where live cell observation is conducted using the microscope apparatus of the first embodiment. It would be completely identical in cases where the live cell observation were conducted using the microscope apparatuses of the second to the fourth embodiments.

FIG. 12 schematically shows a cell nucleus 100, and a microtubule network composed of numerous microtubules 101 extending from the surface of the cell nucleus 100. The dotted line in the drawing illustrates the surface of the cell nucleus 100, and the numerous microtubules 101 extend outwardly from the pertinent surface.

As the microtubules 101 are very concentrated in the vicinity of the surface of the cell nucleus 100, the density of the fluorescent material that adheres to the microtubules 101 in this concentration region is relatively high. Moreover, as tissue that produces microtubules 101 exists in abundance at the surface of the cell nucleus 100, the density of the fluorescent material further increases when fluorescent material adheres to the pertinent issue. On the other hand, as the microtubules 101 are sparse at positions that are distant from the cell nucleus 100, the density of fluorescent material is markedly lower when compared to the vicinity of the surface of the cell nucleus 100.

In the case where live cell observation is conducted by the microscope apparatus 10 of the first embodiment, there is also sequential performance of the distribution measurement step S101, the irradiation intensity setting step S102, and the picture image formation step S103, which are shown in FIG. 2. As a result, a live cell picture image of high resolution is obtained.

The operations of the distribution measurement step S101 and the irradiation intensity setting step S102 are identical to those of the first embodiment. That is, in the distribution measurement step S101, after operations which irradiate a sample with activating light L2 of uniform intensity, operations are performed which obtain a first fluorescent picture image by irradiating the sample with exciting light L1, and a two-dimensional intensity distribution is computed with respect to the pertinent first fluorescent picture image.

In the irradiation intensity setting step S102, a two-dimensional intensity map of irradiation intensities of the activating light L2 is prepared based on the two-dimensional luminance distribution. The prepared two-dimensional intensity map is stored in the memory 16.

In the two-dimensional intensity map for the case of observation of the live cell shown in FIG. 12, the irradiation intensity of activating light L2 is set relatively low in regions that are near the surface of the cell nucleus 100 where the microtubules 101 are concentrated, and the irradiation intensity of activating light L2 is set relatively high in regions that are distant from the cell nucleus 100 where the microtubules 101 are sparse.

Next, in step S14 of the picture image formation step S103, the sample is irradiated with activating light L2 using the two-dimensional intensity map prepared as described above. That is, based on the aforementioned two-dimensional intensity map, irradiation is conducted with activating light L2 of relatively low intensity in regions where the fluorescent material exists at high density, while irradiation with activating light L2 of relatively high intensity is conducted in regions where the fluorescent material exists at low density. As a result, the density of the activated fluorescent material is leveled across the entire view field.

Next, in step S15, the sample is irradiated with exciting light L1, and a second fluorescent picture image is obtained by using the camera 34 to photograph the fluorescence emitted from the fluorescent material in an activated condition. As in the first embodiment, in the case also of the present embodiment, a second fluorescent picture image is obtained in which fluorescent bright spots exist at approximately uniform density, as in the second fluorescent picture image E2 shown in FIG. 6. The obtained second fluorescent picture image is stored in the memory 16 in step S16.

Next, in step S17, the termination of image pickup is assessed, and in the case where image pickup has not terminated, return to step S14 occurs, and operations which irradiate the sample with activating light L2 are again conducted. By means of this irradiation with activating light L2, the unfaded fluorescent material is activated. Subsequently, the operations which obtain and store second fluorescent picture images in steps S15 and S16 are performed.

In the case where live cell observation is conducted, the image pickup speed of second fluorescent picture images from steps S14-S17 is set comparatively high—for example, second fluorescent picture images are obtained on the order of 500 per second. Over a total measured time of several minutes, from several tens of thousands to 200,000 fluorescent picture images are obtained.

When steps S14-S16 have been repetitively performed to the preset number of times, it is determined in step S17 that image pickup has terminated, and transition to step S18 occurs.

In step S18, a sample picture image is prepared from the obtained second fluorescent picture images, and in the case of live cell observation, chronological picture images are prepared for the purpose of displaying over time the movements of the microtubules 101 and the like. Specifically, second fluorescent picture images arranged in a measured time sequence are compartmentalized by a prescribed time interval or prescribed number of picture images in a chronological manner, and a chronological picture image is produced in which the second fluorescent picture images are superimposed in each compartment. For example, operations are performed in which second fluorescent picture images are chronologically compartmentalized in sets of 250 picture images, and a single chronological picture image is prepared by superimposing these 250 picture images. As a result, in the case where, for example, measurement is conducted for 3 minutes at 500 picture images per second, 360 chronological picture images are prepared from 90,000 fluorescent picture images.

The prepared chronological picture images are continuously displayed on a monitor (display apparatus) that is connected to the microscope apparatus. By this means, movements of the microtubules 101 and the like are expressed by animation in high-resolution picture images. With respect to the display method of the chronological picture images, one may adopt an arbitrarily method. For example, one may adopt a method wherein display is conducted while the colors of the dots that compose the picture images change from a blue system to a red system or the like in conjunction with the passage of time, and so on.

In the case where live cell observation is conducted in the manner of the present embodiment, it is possible to obtain a vivid chronological picture image by obtaining second fluorescent picture images while modulating the activating light L2 based on a two-dimensional intensity map.

Specifically, as there is a large difference in the degree of concentration of the microtubules 101 near the surface of the cell nucleus 100 and at positions distant from the cell nucleus 100 shown in FIG. 12, when, for example, irradiation is uniformly conducted with the activating light L2 at an irradiation intensity adjusted to regions where the microtubules 101 are concentrated, fluorescent bright spots are scarcely observed, and the movement of microtubules 101 is not at all to be seen in the regions on the distal side of the microtubules 101. On the other hand, when irradiation is uniformly conducted with the activating light L2 at an irradiation intensity adjusted to the density of fluorescent material on the distal side of the microtubules 101, the picture image is distorted, and becomes invisible, because fluorescent bright spots near the surface of the cell nucleus 100 are too numerous. Consequently, with this observation method, optimal analysis can be conducted only in specific portions within the view field.

In contrast, in the present embodiment, as irradiation is conducted with activating light L2 at respectively optimal irradiation intensities relative to regions with differing densities of fluorescent material, a vivid picture image can be obtained extending from the vicinity of the surface of the cell nucleus 100 to the distal portions of the microtubules 101, enabling observation of wide-ranging movements of the microtubules 101 over time.

In the case where live cell observation is conducted, as the cells under observation move, it is advisable to adopt the observation method of the third aspect described in the preceding fifth embodiment, and to obtain second fluorescent picture images while updating the two-dimensional intensity map as necessary. For example, it is advisable to update the two-dimensional intensity map whenever the second fluorescent picture images required for preparation of a single chronological picture image have been obtained. By this means, it is possible to modulate the activating light L2 based on two-dimensional intensity maps that correspond to changes in distribution of the fluorescent material due to movement of the cells, and to obtain second fluorescent picture images in which the distribution of fluorescent bright spots has been leveled.

Seventh Embodiment

In the foregoing first to sixth embodiments, in step S14, a sample was irradiated with activating light L2 (STORM/PALM) or exciting light L1 (dSTORM) modulated based on a two-dimensional intensity map, but it is also possible to fix the irradiation intensity of the activating light L2 or exciting light L1 within the view field.

Specifically, in step S11 of the distribution measurement step S101, a first fluorescent picture image is obtained, and a two-dimensional intensity distribution is computed in the first fluorescent picture image in the following step S12.

In the irradiation intensity setting step S102, an irradiation intensity of the activating light L2 is set based on the maximum value of radiation intensity in the two-dimensional intensity distribution. That is, the irradiation intensity of the activating light L2 is set so that an appropriate fluorescent bright spot interval (3 times or more the optical resolution) is obtained in the region where radiation intensity is largest.

Next, in the picture image formation step S103, there is repetitive performance to a prescribed number of times of a step S14 in which the sample is irradiated with activating light L2 at the irradiation intensity that was set in the irradiation intensity setting step S102, and a step S15 in which a second fluorescent picture image is obtained by irradiating the sample with exciting light L1, and from several hundred to several tens of thousands of second fluorescent picture images are obtained. Subsequently, in step S18, a sample picture image is generated from the second fluorescent picture images.

In the present embodiment, by setting the irradiation intensity of the activating light L2 that irradiates the sample in the picture image formation step S103 based on a maximum value of radiation intensity observed in the distribution measurement step S101, it is possible to prevent distortion of picture images due to excessive narrowness of the interstices of fluorescent bright spots in the second fluorescent picture images.

Moreover, as there is no need for the spatial light modulator 62 in order to vary irradiation intensities of activating light L2 within the view field, it is possible to inexpensively configure the microscope.

What is claimed is:

1. A microscope apparatus comprising:
   a first optical system configured to irradiate an activating light which actives a part of a plurality of fluorescent material included in a sample to a state capable of emitting a fluorescence,
   a second optical system configured to irradiate an exciting light that excites at least a part of the activated fluorescent material and that causes the fluorescence to emit,
   an imager, and
   a controller configured to:
      calculate fluorescent intensity distribution information of a fluorescent image captured by the imager by classifying a fluorescent intensity distribution of the fluorescent image captured by the imager into multiple levels by prescribed ranges of fluorescent intensity, and
      control capture of another fluorescent image by setting different intensities of the activating light for each of a plurality of regions of the sample so that different ones of the regions are irradiated with the different intensities of the activating light, the different intensities being set based on the calculated levels, and by setting an intensity of the exciting light to a predetermined intensity.

2. The microscope apparatus according to claim 1, further comprising:
   a spatial light modulator configured to adjust the intensities of the activating light in the regions.

3. The microscope apparatus according to claim 1, further comprising:
an optical element configured to modulate intensity of the activating light to be the different intensities for each of the plurality of regions of the sample, and
a scanner configured to scan above the sample with the modulated activating light.

4. The microscope apparatus according to claim 1, wherein the fluorescent intensity distribution information has a relatively low intensity at a region having a relatively high concentration of the fluorescent material, and has a relatively high intensity at a region having a relatively low concentration of the fluorescent material.

5. The microscope apparatus according to claim 1, wherein at least a part of the first optical system also is a part of the second optical system.

6. The microscope apparatus according to claim 1, wherein the controller sets the different intensities by tonally inverting a fluorescent intensity distribution of the fluorescent image captured by the imager.

7. The microscope apparatus according to claim 1, wherein the controller:
calculates position information of an image of the fluorescent material by using at least a part of a plurality of fluorescent images captured by the imager, and
generates a sample fluorescent image by using at least a part of the calculated position information.

8. A method comprising:
irradiating an activating light which actives a part of a plurality of fluorescent material included in a sample to a state capable of emitting a fluorescence,
irradiating an exciting light that excites at least a part of the activated fluorescent material and that causes the fluorescence to emit,
calculating a fluorescent intensity distribution information of a captured fluorescent image by classifying a fluorescent intensity distribution of the captured fluorescent image into multiple levels by prescribed ranges of fluorescent intensity, and
capturing another fluorescent image by irradiating the activating light to the sample with different intensities for each of a plurality of regions of the sample so that different ones of the regions are irradiated with the different intensities of the activating light, the different intensities being set based on the calculated levels, and by irradiating an exciting light to the sample with a predetermined intensity.

9. The method according to claim 8, further comprising:
adjusting the intensities of the activating light in the regions by using a spatial light modulator.

10. The method according to claim 8, further comprising:
modulating intensity of the activating light to be the different intensities for each of the plurality of regions of the sample, and
scanning above the sample with the modulated activating light.

11. The method according to claim 8, wherein the fluorescent intensity distribution information has a relatively low intensity at a region having a relatively high concentration of the fluorescent material, and has a relatively high intensity at a region having a relatively low concentration of the fluorescent material.

12. The method according to claim 8, further comprising:
setting the different intensities by tonally inverting a fluorescent intensity distribution of the captured fluorescent image.

13. The method according to claim 8, further comprising:
calculating position information of the image of a fluorescent material by using at least a part a plurality of captured fluorescent images, and
generating a sample fluorescent image by using at least a part of the calculated position information.

14. A microscope apparatus comprising:
a first optical system configured to irradiate an activating light which actives a part of a plurality of fluorescent material included in a sample to a state capable of emitting a fluorescence,
a second optical system configured to irradiate an exciting light that excites at least a part of the activated fluorescent material and that causes the fluorescence to emit,
an imager, and
a controller configured to:
calculate fluorescent intensity distribution information of a captured fluorescent image by classifying a fluorescent intensity distribution of the fluorescent image captured by the imager into multiple levels by prescribed ranges of fluorescent intensity,
set different intensities of the activating light for each of a plurality of regions of the sample so that different ones of the regions are irradiated with the different intensities of the activating light, the different intensities being set based on the calculated levels,
set an intensity of the exciting light to a predetermined intensity,
control the first optical system to control the activating light to irradiate at the set different intensities, and
control the second optical system to control the exciting light to irradiate at the predetermined intensity, and the imager to capture another fluorescent image.

15. A microscope apparatus comprising:
a first optical system configured to irradiate an activating light which actives a part of a plurality of fluorescent material included in a sample to a state capable of emitting a fluorescence,
a second optical system configured to irradiate an exciting light that excites at least a part of the activated fluorescent material and that causes the fluorescence to emit,
an imager, and
a controller configured to:
calculate fluorescent intensity distribution information of a captured fluorescent image by classifying a fluorescent intensity distribution of the fluorescent image captured by the imager into multiple levels by prescribed ranges of fluorescent intensity,
control the first optical system to irradiate the activating light at different intensities for each of a plurality of regions of the sample so that different ones of the regions are irradiated with the different intensities of the activating light, the different intensities being set based on the calculated levels,
control the second optical system to irradiate the exciting light at a predetermined intensity, and
control the imager to capture another fluorescent image.

\* \* \* \* \*